(12) United States Patent
Gilam et al.

(10) Patent No.: US 10,568,901 B2
(45) Date of Patent: Feb. 25, 2020

(54) MICRO-RNA FOR THE TREATMENT OF MALIGNANT SOLID TUMORS AND METASTASIS

(71) Applicants: RAMOT AT TEL AVIV UNIVERSITY LTD., Tel Aviv (IL); TEL HASHOMER MEDICAL RESEARCH INFRASTRUCTURE AND SERVICES LTD., Ramat-Gan (IL)

(72) Inventors: Avital Gilam, Ra'anana (IL); Noam Shomron, Herzelia (IL); Eitan Friedman, Tel Aviv (IL)

(73) Assignees: TEL HASHOMER MEDICAL RESEARCH INFRASTRUCTURE AND SERVICES LTD., Ramat-Gan (IL); RAMOT AT TEL AVIV UNIVERSITY LTD., Tel-Aviv (IL)

( * ) Notice: Subject to any disclaimer, the term of this patent is extended or adjusted under 35 U.S.C. 154(b) by 43 days.

(21) Appl. No.: 15/744,086

(22) PCT Filed: Jul. 14, 2016

(86) PCT No.: PCT/IL2016/050759
§ 371 (c)(1),
(2) Date: Jan. 12, 2018

(87) PCT Pub. No.: WO2017/009837
PCT Pub. Date: Jan. 19, 2017

(65) Prior Publication Data
US 2018/0193374 A1 Jul. 12, 2018

Related U.S. Application Data

(60) Provisional application No. 62/192,588, filed on Jul. 15, 2015.

(51) Int. Cl.
*A61K 31/7105* (2006.01)
*C12N 15/113* (2010.01)
*A61K 31/713* (2006.01)
*A61P 35/04* (2006.01)

(52) U.S. Cl.
CPC ........ *A61K 31/7105* (2013.01); *A61K 31/713* (2013.01); *A61P 35/04* (2018.01); *C12N 15/113* (2013.01); *C12N 2310/141* (2013.01)

(58) Field of Classification Search
CPC ... A61K 31/713; A61K 31/7105; A61P 35/04; C12N 15/113; C12N 2310/14; C12N 2310/141
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

2011/0021607 A1 1/2011 Clarke
2014/0088170 A1 3/2014 Shi

FOREIGN PATENT DOCUMENTS

| WO | 2010056737 A2 | 5/2010 | |
|---|---|---|---|
| WO | 2010061396 A1 | 6/2010 | |
| WO | 2012005572 A1 | 1/2012 | |
| WO | WO-2012005572 A1 * | 1/2012 | ........... C12N 15/111 |

OTHER PUBLICATIONS

Li et al (Breast Cancer Research, vol. 16, p. 473 (pp. 1-17) (2014)) (Year: 2014).*
Sachdeva et al (J. Clin. Invest., vol. 124, No. 10, (2014)) (Year: 2014).*
Hu et al (PLoS One, DOI.10.1371, 13 pages) (May 14, 2015)) (Year: 2015).*
Zhang et al (Oncology Reports, vol. 31, pp. 1357-1363 (2014)) (Year: 2014).*
Mao et al SCJD, vol. 21, No. 34, pp. 3775-3782 (2013)) (Year: 2013).*
Bao et al., "Polymorphisms inside MicroRNAs and MicroRNA Target Sites Predict Clinical Outcomes in Prostate Cancer Patients Receiving Androgen-Deprivation Therapy", Clinical Cancer Research, pp. 928-936, vol. 17(No. 4) (Feb. 2011).
Griffiths-Jones et al., "miRBase: tools for microRNA genomics", Nucleic acids research, vol. 36,pp. D154-D158(suppl_1), (Oct. 2007).
Li et al., "MiR-1831-96/-182 cluster is up-regulated in most breast cancers and increases cell proliferation and migration", Breast cancer research, pp. 1-17, vol. 16(No. 6), 473 (Nov. 2014).
Ofek et al., "In vivo delivery of small interfering RNA to tumors and their vasculature by novel dendritic nanocarriers", The FASEB Journal, vol. 24(No. 9), pp. 3122-3134 (Sep. 2010).
Peer et al., "Systemic leukocyte-directed siRNA delivery revealing cyclin D1 as an anti-inflammatory target", Science, vol. 319(5863), pp. 627-630 (Feb. 2008).
Sarfati et al.,"Targeting of polymeric nanoparticles to lung metastases by surface-attachment of YIGSR peptide from laminin", Biomaterials, vol. 32(No. 1), pp. 152-161 (Oct. 2010).
Assal et al., (2015) A pleiotropic effect of the single clustered hepatic metastamiRs miR-96-5p and miR-182-5p on insulin-like growth factor II, insulin-like growth factor-1 receptor and insulin-like growth factor-binding protein-3 in hepatocellular carcinoma. Mol Med Rep 12(1): 645-650.
Feng et al., (2014) HERG1 functions as an oncogene in pancreatic cancer and is downregulated by miR-96. Oncotarget 5(14): 5832-5844.
Gilam et al., (2016) Local microRNA delivery targets Palladin and prevents metastatic breast cancer. Nat Commun 7: 12868; 14 pages.
Hu et al., (2015) The Downregulation of MiR-182 Is Associated with the Growth and Invasion of Osteosarcoma Cells through the Regulation of TIAM1 Expression. PLoS One 10(5): e0121175; 13 pages.

(Continued)

*Primary Examiner* — Jane J Zara
(74) *Attorney, Agent, or Firm* — Browdy and Neimark, PLLC

(57) ABSTRACT

Provided are compositions and methods for treating cancer, particularly solid tumors, and cancer metastasis, using micro-RNAs mi R-96 and/or mi R-182.

23 Claims, 21 Drawing Sheets

Specification includes a Sequence Listing.

(56) References Cited

OTHER PUBLICATIONS

Huang et al., (2014) miR-96 functions as a tumor suppressor gene by targeting NUAK1 in pancreatic cancer. Int J Mol Med 34(6): 1599-1605.
Huynh et al., (2011) Efficient in vivo microRNA targeting of liver metastasis. Oncogene 30(12): 1481-1488.
Mao et al., (2013) Role of miR-96 in invasion and migration of gastric cancer cells. World Chinese Journal of Digestology 21(34): 3775-3782. Abstract.
Sachdeva et al., (2014) MicroRNA-182 drives metastasis of primary sarcomas by targeting multiple genes. J Clin Invest 124(10): 4305-4319.
Wei et al., (2015) Roles of miR-182 in sensory organ development and cancer. Thorac Cancer 6(1): 2-9.
Yu et al., (2010) miRNA-96 Suppresses KRAS and Functions as a Tumor Suppressor Gene in Pancreatic Cancer. Cancer Res 70(14): 6015-6025.
Zhang et al., (2014) miR-96 promotes tumor proliferation and invasion by targeting RECK in breast cancer. Oncol Rep 31(3): 1357-1363.

\* cited by examiner

TarDel     *TGGAATTT*------------------------------------------------------------------
PALLD-G   *TGGAATTT*AAGATACCATACACAGTCTCTCATGGACCTATCTCTA
PALLD-C   *TGGAATTT*AAGATACCATACACAGTCTCTCATGGACCTATCTCTA

TarDel    ------------------------------------------------------------TTCTGAATG
PALLD-G   TTGTAGAATTATGACTTATGTCTTACTTGGCAAATTTTTCTGAATG
PALLD-C   TTGTAGAATTATGACTTATGTCTTACTTGCCAAATTTTTCTGAATG
    miR-182   3' UCACACUCAAGAUGGUAACGGUUU 5'
    miR-96    3' UCGUUUUACACGAUC-ACGGUUU 5'
                                        ↑
                            rs1071738 SNP

Figure 1

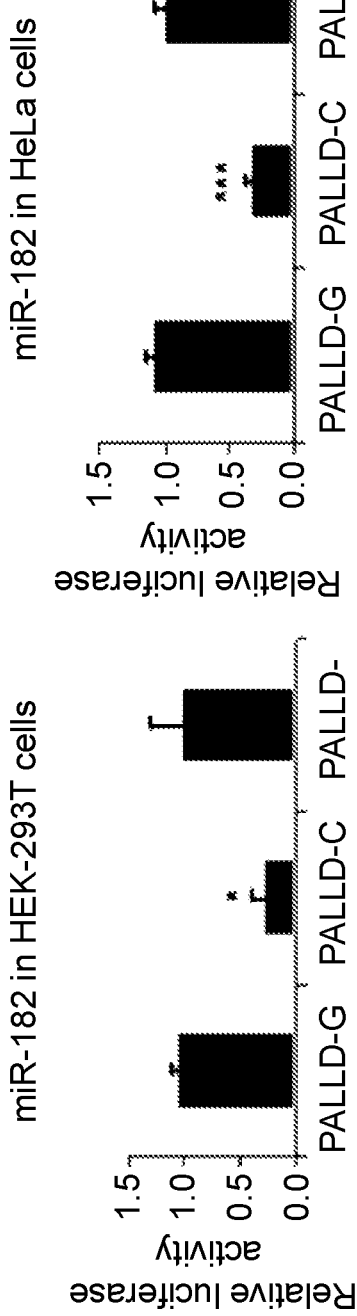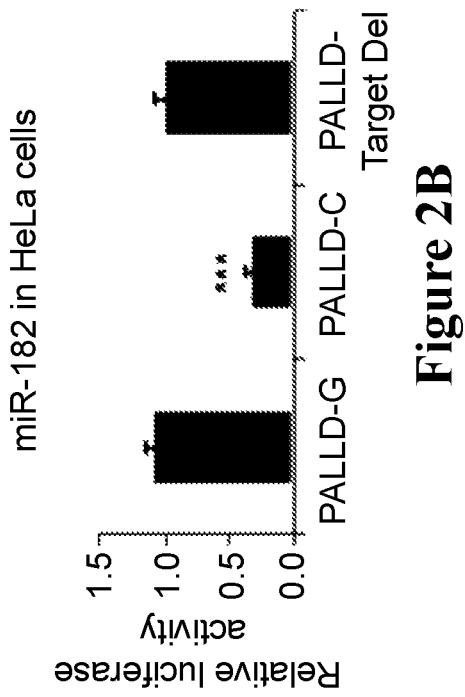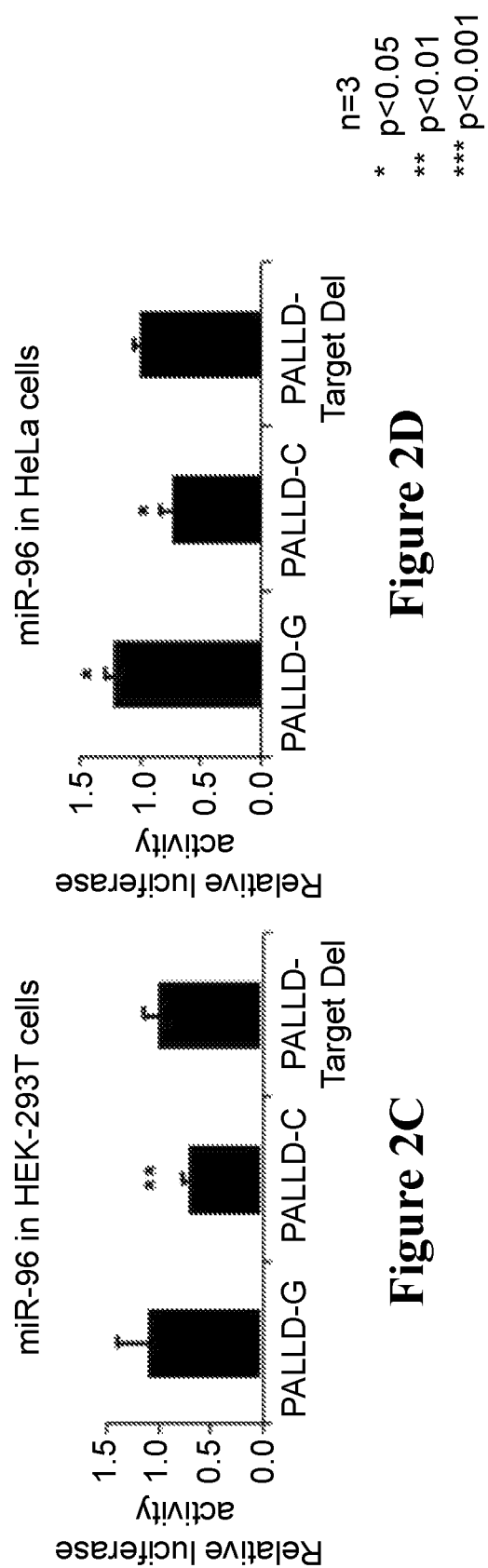

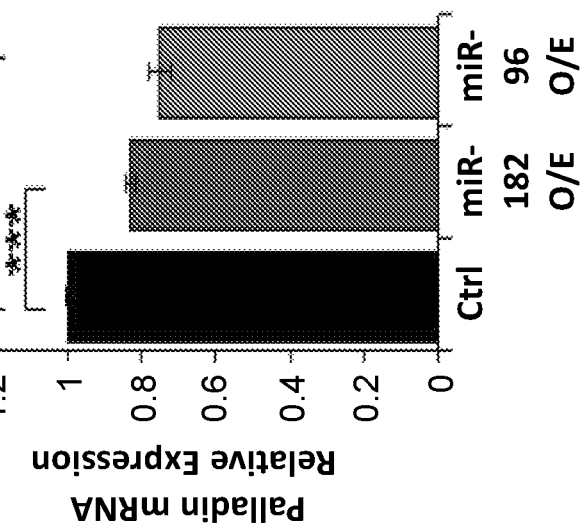
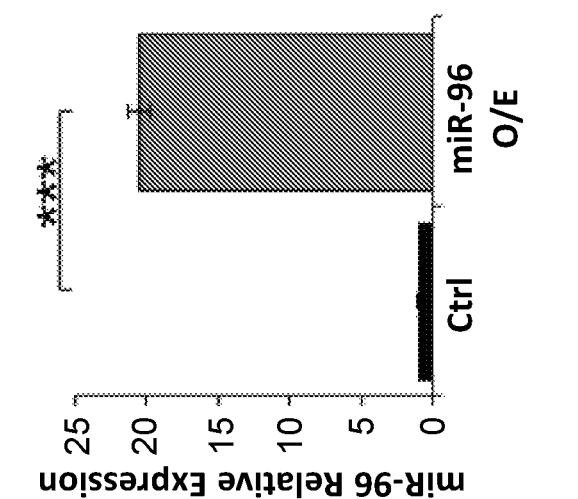
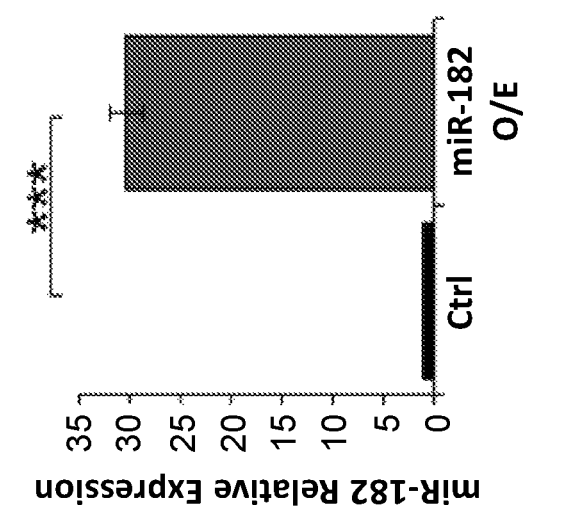
Figure 3A
Figure 3B
Figure 3C

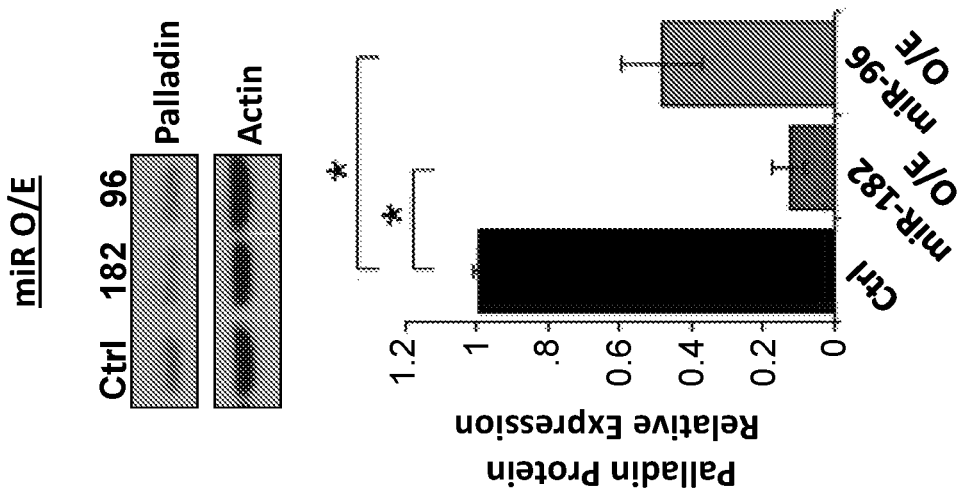
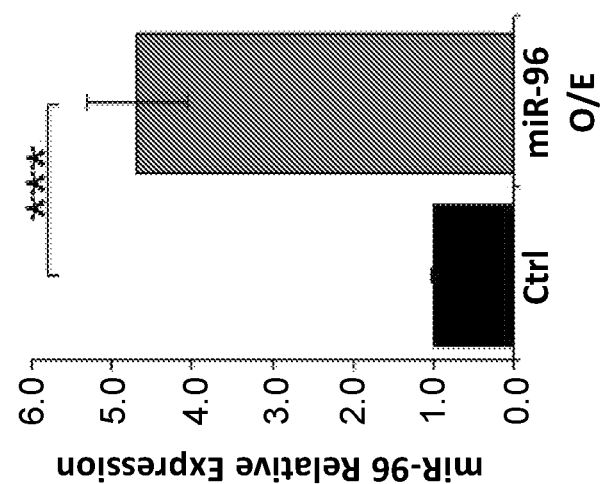
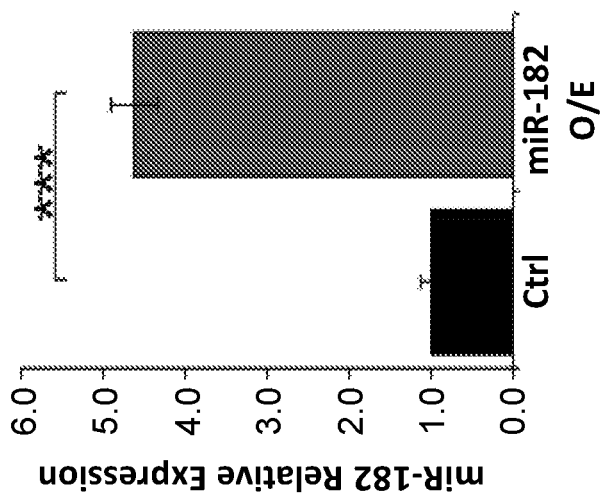
Figure 3F
Figure 3G
Figure 3H

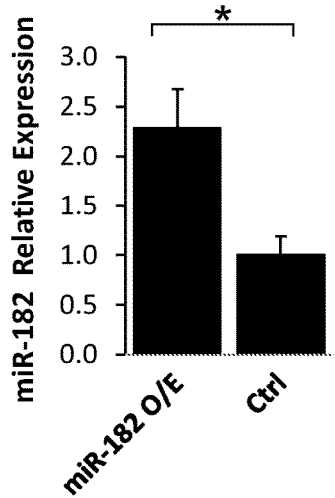
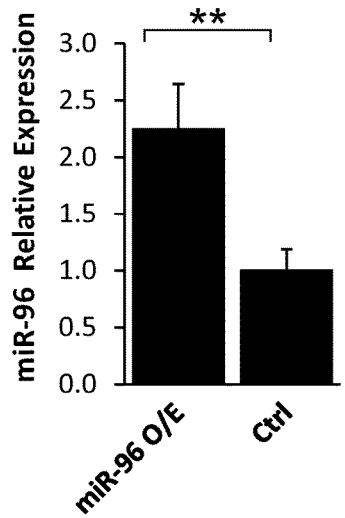
Figure 8A             Figure 8B
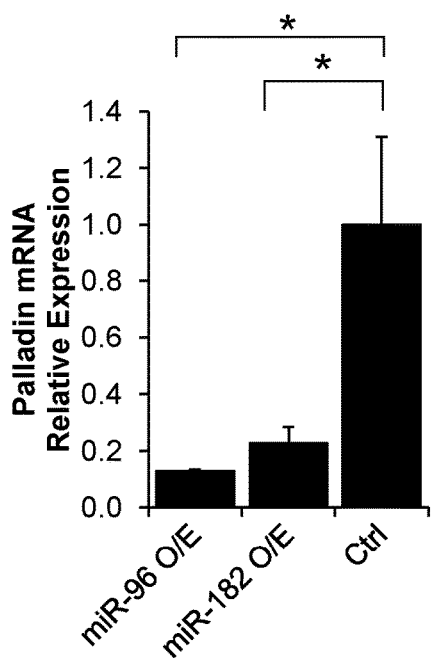
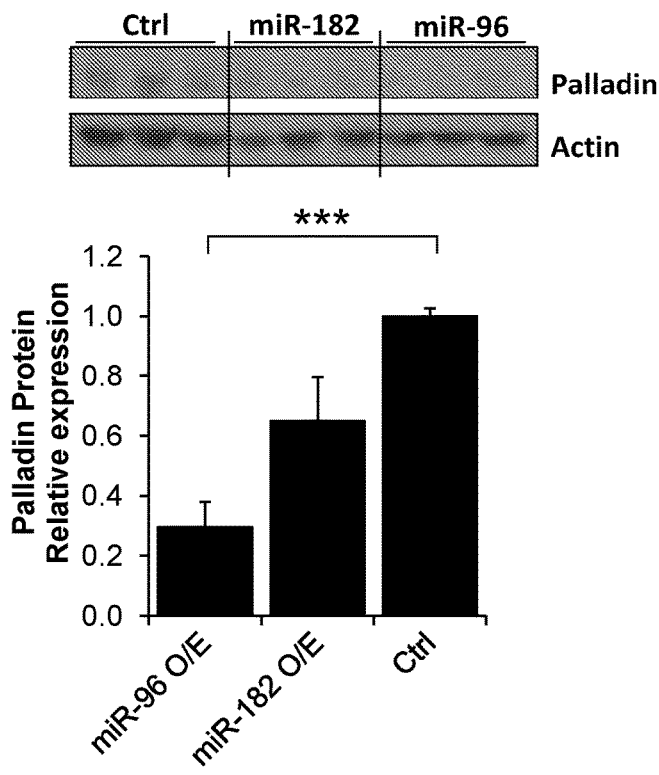
Figure 8C             Figure 8D

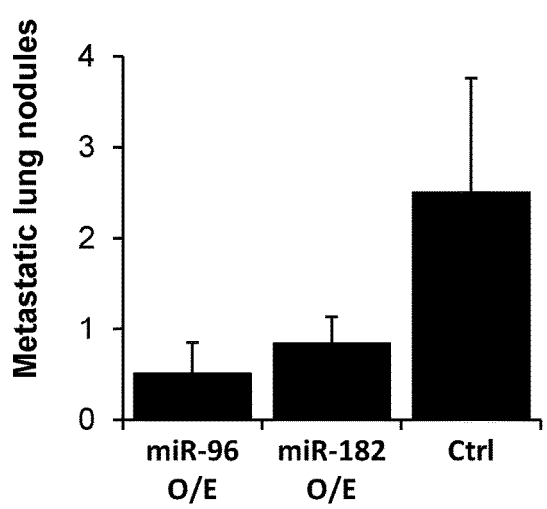
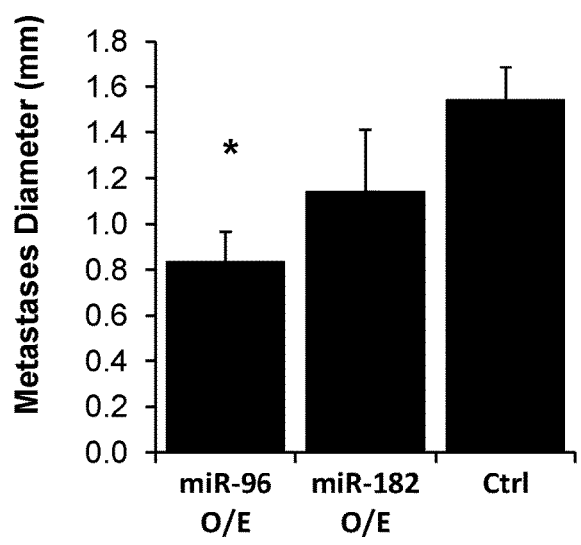
Figure 10B                    Figure 10C

SEQUENCE LISTING

<160> NUMBER OF SEQ ID NOS: 19

<210> SEQ ID NO 1

```
<211> LENGTH: 23
<212> TYPE: RNA
<213> ORGANISM: Homo sapiens

<400> SEQUENCE: 1
uuuggcacua gcacauuuuu gcu                                            23

<210> SEQ ID NO 2
<211> LENGTH: 477
<212> TYPE: RNA
<213> ORGANISM: Homo sapiens

<400> SEQUENCE: 2
acugugaaca gucucaguca gugaauuacc gaagggccau aaacagagca gagacagauc    60
cacgagggcc uccggagcac cuuacccacu ucugccuuga gugcuccuag acgucggaaa   120
caggcugcuu ccaagggugc agggaugcaa ggccccucgu ccagugeugc cccagagagc   180 ccgcaccagu gccaucugcu uggccgauuu uggcacuagc acauuuuugc uugugucucu   240
ccgcucugag caaucaugug cagugccaau augggaaaag caggacccgc agcugcgucc   300
gccuccccug cauccuugug ucagggcccc agccugcucc uccuccaagg cuccucaccg   360
ccuccccagc ccaucuggcu cagcugcugu gugagggccc agcgcugguuog ggcagccaga   420 ucgccuuaca cugccugggg ccacgguaga gcugggagcc cagcaaucug agcuggg     477

<210> SEQ ID NO 3
<211> LENGTH: 78
<212> TYPE: RNA
<213> ORGANISM: Homo sapiens

<400> SEQUENCE: 3
uggccgauuu uggcacuagc acauuuuugc uugugucucu ccgcucugag caaucaugug    60
cagugccaau augggaaa                                                  78

<210> SEQ ID NO 4
<211> LENGTH: 24
<212> TYPE: RNA
<213> ORGANISM: Homo sapiens

<400> SEQUENCE: 4
uuuggcaaug guagaacuca cacu                                           24

<210> SEQ ID NO 5
<211> LENGTH: 510
<212> TYPE: RNA
<213> ORGANISM: Homo sapiens

<400> SEQUENCE: 5
ggagaggagg gggcugagga gggaccggga ccagcaggaa gggggacugu ggggpuugggc    60 cuccacacca gggcgacccu gcaggaagga ccuugucgca guugcgggga ugggcgccuc   120
uguccuggcc cugccuggac cauccuaacu gucucugucu cuuccucagc acagaccgag   180
gccuccccag cuccuggggg gagcugcuug ccucccccg uuuuuggcaa ugguagaacu    240
cacacuggug agguaacagg auccgguggu ucuagacuug ccaacuaugg ggcgaggacu   300
cagccggcac ccugugcaca gccagcgagg gaagggccgg ccaugcugga ccugcuguuc   360
uccgcgagga aggaggggac ucaggucccg gacugcuggg uaguggcaga gggcagguge   420 agcuggaagu gacacucugu guuucccgc auccccuga ggucacaggu ccucaaguca    480
gcugggaagc cguucucugg ccccucagggg                                   510
```

<210> SEQ ID NO 6
<211> LENGTH: 110
<212> TYPE: RNA
<213> ORGANISM: Homo sapiens

<400> SEQUENCE: 6
gagcugcuug ccucccccg uuuuuggcaa ugguagaacu cacacuggug agguaacagg    60
auccgguggu ucuagacuug ccaacuaugg ggcgaggacu cagccggcac              110

<210> SEQ ID NO 7
<211> LENGTH: 509
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<222> LOCATION: (460)..(460)
<223> OTHER INFORMATION: n is a, c, g, or t

<400> SEQUENCE: 7
gacctccata gaagattcta gagctagcga attcgtggtc ctctccgtgc taccgcactg    60
tgggtacttg ctgctccagc agggcacgca cagcgtccgt ggagggaaag ccttttccc    120 cacttcttaa ccttcactga gagggtggtt ggggtctgtt tcactccatg tgtcctagat   180
cctgtgctac agaccttcct ttctgtcctc ccgtcttgga cctcagtcct gggggctcca   240
aagtgctgtt cgtgcaggta gtgtgattac ccaacctact gctgagctag cacttcccga   300
gcccccggga cacgttctct ctgccaattg tcttcttggc tgagctcccc aagctccatc   360
tgtcatgctg gggagcccag tggcgttcaa aagggtctgg tctccctcac aggacagctg   420
aactccggga ctggccagtg ttgagaggcg agacttggn aaattgctgg acgctgcggc    480
cgcaaggatc tgcgatcgct ccggtgccc                                     509

<210> SEQ ID NO 8
<211> LENGTH: 304
<212> TYPE: DNA
<213> ORGANISM: Artificial Sequence
<220> FEATURE:
<223> OTHER INFORMATION: Plasmid

<400> SEQUENCE: 8
gacctccata gaagattcta gagctagcga attcctccta aaaccaccct aactgcttct    60
tcttcagcat aggcttactg gtctggctgc tggaggcctc ccaccatttt tggcaatggt   120
agaactcaca ccggtaaggt aatgggaccc ggtggttcta gacttgccaa ctatggtgta   180
agtgctgagc tgctgaaggt ctgcaccgtg ccggaacctg ccgatcacca ggaaggagag   240
gggactcctg tctccagacc accaggcagt gcggccgcaa ggatctgcga tcgctccggt   300
gccc                                                                304

<210> SEQ ID NO 9
<211> LENGTH: 25
<212> TYPE: DNA
<213> ORGANISM: Mus musculus

<400> SEQUENCE: 9
tttggcaatg gtagaactca caccg                                          25

<210> SEQ ID NO 10

```
<211> LENGTH: 75
<212> TYPE: DNA
<213> ORGANISM: Mus musculus

<400> SEQUENCE: 10 accattttg gcaatggtag aactcacacc ggtaaggtaa tgggacccgg tggttctaga    60
cttgccaact atggt                                                    75

<210> SEQ ID NO 11
<211> LENGTH: 316
<212> TYPE: DNA
<213> ORGANISM: Artificial Sequence
<220> FEATURE:
<223> OTHER INFORMATION: Plasmid

<400> SEQUENCE: 11
gacctccata gaagattcta gagctagcga attcggtgcc agggtacaaa gacctcctct    60
gctccttccc cagagggcct gttccagtac catctgcttg ccgattttg gcactagcac   120 attttgctt gtgtctctcc gctgtgagca atcatgtgta gtgccaatat gggaaaagcg   180
ggctgctgcg ccacgttca cctcccccgg catcccaggg tctgtgtgtc tcactggctc   240
cctggcccat ctggcttact gctgggtgag gagggtacag ccgcggccgc aaggatctgc   300
gatcgctccg gtgccc                                                  316

<210> SEQ ID NO 12
<211> LENGTH: 23
<212> TYPE: DNA
<213> ORGANISM: Mus musculus

<400> SEQUENCE: 12
tttggcacta gcacattttt gct                                           23

<210> SEQ ID NO 13
<211> LENGTH: 106
<212> TYPE: DNA
<213> ORGANISM: Mus musculus

<400> SEQUENCE: 13
ccagtaccat ctgcttggcc gattttggca ctagcacatt tttgcttgtg tctctccgct    60
gtgagcaatc atgtgtagtg ccaatatggg aaaagcgggc tgctgc                 106

<210> SEQ ID NO 14
<211> LENGTH: 5
<212> TYPE: PRT
<213> ORGANISM: Artificial Sequence
<220> FEATURE:
<223> OTHER INFORMATION: Peptide

<400> SEQUENCE: 14

Tyr Ile Gly Ser Arg
1               5

<210> SEQ ID NO 15
<211> LENGTH: 91
<212> TYPE: DNA
<213> ORGANISM: Homo sapiens

<400> SEQUENCE: 15
tggaatttaa gataccatac acagtctctc atggacctat ctctattgta gaattatgac    60
ttatgtctta cttggcaaat ttttctgaat g                                  91
```

```
<210> SEQ ID NO 16
<211> LENGTH: 91
<212> TYPE: DNA
<213> ORGANISM: Homo sapiens

<400> SEQUENCE: 16
tggaatttaa gataccatac acagtctctc atggacctat ctctattgta gaattatgac      60
ttatgtctta cttgccaaat ttttctgaat g                                    91

<210> SEQ ID NO 17
<211> LENGTH: 17
<212> TYPE: DNA
<213> ORGANISM: Artificial Sequence
<220> FEATURE:
<223> OTHER INFORMATION: Homo Sapiens

<400> SEQUENCE: 17
tggaattttt ctgaatg                                                    17

<210> SEQ ID NO 18
<211> LENGTH: 21
<212> TYPE: DNA
<213> ORGANISM: Artificial Sequence
<220> FEATURE:
<223> OTHER INFORMATION: Homo Sapiens

<400> SEQUENCE: 18
gctaacctat gaggaaagaa t                                               21

<210> SEQ ID NO 19
<211> LENGTH: 57
<212> TYPE: DNA
<213> ORGANISM: Artificial Sequence
<220> FEATURE:
<223> OTHER INFORMATION: Homo Sapiens

<400> SEQUENCE: 19
ccgggcgcga tagcgctaat aatttctcga gaaattatta gcgctatcgc gctttttt        57
```

MICRO-RNA FOR THE TREATMENT OF MALIGNANT SOLID TUMORS AND METASTASIS

The Sequence Listing in ASCII text file format of 6,504 bytes in size, created on Jan. 10, 2018, with the file name "2018-01-12SequenceListing-GILAM1," filed in the U.S. Patent and Trademark Office on Jan. 12, 2018, is hereby incorporated herein by reference.

FIELD OF THE INVENTION

The present invention relates to a micro-RNA (miRNA)-based treatment of cancer, particularly solid tumors, and metastasis.

BACKGROUND OF THE INVENTION

Malignant solid tumors are masses of abnormal tissue that originate in organs or soft tissues that typically do not include fluid areas and cysts. Different types of solid tumors are named for the type of cells that form them. Examples of solid tumors are sarcomas, carcinomas, and lymphomas. Malignant solid tumors initially grow in the organ of their cellular origin. However, such cancers may spread to other organs through metastatic tumor growth in advanced stages of the disease.

Existing therapies of solid tumors include surgery, radiation, chemotherapy, targeted therapy using e.g., antibodies and in some cases hormone therapy. However, despite improvements in therapeutic interventions, metastasis is still a major cause of mortality in solid tumors.

Tumorigenesis and metastasis is thought to be regulated, inter alia, by tissue specific micro-RNAs (miRNAs or miRs). miRNAs are non-coding RNA molecules of about 21-22 nucleotides in length, which are endogenously expressed either ubiquitously or in a tissue-specific manner and play an important regulatory role in various cellular processes. miRNAs regulate gene expression by binding to complementary sequences in target messenger RNA (mRNA) molecules, typically in untranslated regions (UTRs) thereof, and triggering their repression. MiRNAs were observed to be important for a diverse range of biological processes such as development, differentiation, proliferation, growth, cell cycle and apoptosis.

miR-96 and miR-182 are two miRNAs which are part of a cluster of miRNAs containing miRs-183, 96 and 182. The miR-183/-96/-182 cluster is a highly conserved polycistronic miRNA cluster shown to be abnormally expressed in a variety of tumors.

Li et al. (*Breast Cancer Research*, 2014, 16:473) report that the miR-183/-96/-182 cluster is up-regulated in most breast cancers and increases cell proliferation and migration.

US 2011/0021607 discloses micro-RNA markers of breast cancer stem cells (BCSC), inter alia, micro-RNAs in the 183/-96/-182 cluster. Uses of the markers include use as targets for therapeutic intervention, as targets for drug development, and for diagnostic or prognostic methods relating to breast cancer and BCSC cell populations.

US 2014/0088170 discloses differentially expressed microRNA molecules for the treatment and diagnosis of cancer, particularly identification of several miRNAs that are differentially expressed in glioblastoma stem cells and normal neural stem cells. Among others, differential expression of miR-96 and miR-182 in cancer cells compared to normal cells is disclosed.

There remains a need in the art for effective and specific compositions and methods for treating cancer and cancer metastasis, such as, for example, breast cancer.

SUMMARY OF THE INVENTION

According to some aspects, the present invention provides compositions and methods for effective treatment of malignant solid tumors in a subject, to reduce or even prevent the formation of metastasis, using micro-RNAs, namely miR-96 and/or miR-182.

The present invention is based in part on the finding that over-expression of miR-96 or miR-182 in cancer cells in-vitro resulted in reduced migration and invasion of the cells through a membrane, as compared to over-expression of a control RNA sequence. Over-expression of miR-96 and/or miR-182 in breast cancer cells in an in-vivo model of breast cancer metastasis almost completely abolished metastasis formation compared to a control RNA sequence. Surprisingly, over-expression of just one of the two miRs was sufficient to exert the beneficial anti-metastatic effect. Further improvement may be achieved by using both miR-96 and miR-182.

Further, the present invention discloses for the first time that successful treatment with miR-96 and/or miR-82 depends on the genotype at a specific polymorphic position within a target gene of these miRs, denoted PALLD. The PALLD gene (PALLD Gene ID: 23022, accession No: NG_013376), encoding for palladin protein (Accession No: Q8WX93), which is involved in cytoskeleton rearrangement, has a G/C single nucleotide polymorphism (SNP) within the binding site of miR-96 and miR-182, identified by reference number rs1071738 (dbSNP database). It is now disclosed that the C allele is required for efficient regulation of this gene by the miRs. Without being bound by any particular theory or a mechanism of action, it is contemplated that the miRNA molecules down-regulate palladin expression, and thus inhibit and even completely abolish the ability of the primary tumor to metastasize.

According to one aspect, the present invention provides a method for reducing or preventing cancer metastasis in a subject in need thereof, the method comprising administering to the subject at least one miRNA molecule selected from the group consisting of miR-96 and miR-182, or at least one vector expressing or encoding the same, thereby reducing or preventing cancer metastasis in the subject.

In some embodiments, the subject according to the present invention is typically a human subject diagnosed with cancer. The subject is preferably an individual with the C allele of the polymorphic site within the PALLD gene identified by reference number rs1071738.

In some embodiments, the method further comprises determining that the subject is carrying the C allele of the single nucleotide polymorphism (SNP) rs1071738 prior to administering the at least one miRNA molecule or the at least one vector expressing or encoding the same.

In some embodiments, the subject is at risk of developing metastasis and the administering is carried out prior to metastasis formation. In other embodiments, the subject has already developed metastases and the administering is carried out after metastasis formation.

In some embodiments, the method comprises administering a miR-96 molecule and/or a miR-182 molecule, or vectors expressing or encoding the miR-96 and/or miR-182 molecules. In some embodiments, the miR-96 molecule and the miR-182 molecule, or the vectors expressing or encoding the same, are administered concomitantly. In other embodiments, the miR-96 molecule and the miR-182 molecule, or the vectors expressing or encoding the same, are administered sequentially. In some embodiments, the miR-96 and the miR-182 are expressed or encoded by a single vector.

In some embodiments, the miR-96 is a mature miR-96 as set forth in SEQ ID NO:1 (5'-UUUGGCACUAGCA-CAUUUUUGCU).

In other embodiments, the miR-96 is a precursor of miR-96. In some embodiments, the precursor of miR-96 is a pri-miRNA as set forth in SEQ ID NO: 2.

In other embodiments, the precursor of miR-96 is a pre-miRNA as set forth in SEQ ID NO: 3.

In some embodiments, the miR-182 is a mature miR-182 as set forth in SEQ ID NO: 4 (5'-UUUGGCAAUGGUA-GAACUCACACU).

In other embodiments, the miR-182 is a precursor of miR-182. In some embodiments, the precursor of miR-182 is a pri-miRNA as set forth in SEQ ID NO: 5. In other embodiments, the precursor of miR-182 is a pre-miRNA as set forth in SEQ ID NO: 6.

In some embodiments, the at least one miRNA molecule or vector expressing or encoding the same is formulated in a pharmaceutical composition with a pharmaceutically acceptable carrier.

In some embodiments, the administering is administering systemically. In other embodiments, the administering is administering locally. In some embodiments, administering locally is administering into a tumor. In additional embodiments, administering locally is administering into a space or cavity adjacent to a tumor. In other embodiments, administering locally is administering into a space or cavity formed after tumor resection.

According to another aspect, the present invention provides a pharmaceutical composition comprising at least one miRNA molecule selected from the group consisting of miR-96 and miR-182, or at least one vector expressing or encoding the same, for use in reducing or preventing breast cancer metastasis.

In some embodiments, the pharmaceutical composition is formulated for systemic administration. In other embodiments, the pharmaceutical composition is formulated for local administration. In some embodiments, the pharmaceutical composition is formulated for intra-tumor administration.

According to yet another aspect, the present invention provides a miRNA molecule selected from the group consisting of miR-96 and miR-182, or a vector expressing or encoding the same, for use in reducing or preventing cancer metastasis.

Further provided is the use of at least one miRNA molecule selected from the group consisting of miR-96 and miR-182, or at least one vector expressing or encoding the same, for the preparation of a medicament for reducing or preventing cancer metastasis.

These and further aspects and features of the present invention will become apparent from the detailed description, examples and claims which follow.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 1. Sequence alignment of three constructs generated for a reporter assay described in Example 1 having different alleles of the 3'UTR of PALLD gene: the C allele ("PALLD-C" SEQ ID NO:16), the G allele ("PALLD-G" SEQ ID NO:15) and a negative control 3'UTR in which the target site is deleted (Target-deletion, "TarDel" SEQ ID NO:17). The position of SNP rs1071738 is marked by an arrow. Human miR-96 (SEQ ID NO:1) and miR-182 (SEQ ID NO:4) are shown aligned with their binding site within PALLD. The "seed" sequence of the miRs is underlined.

FIGS. 2A-D. Regulation of palladin by miR-182 (FIGS. 2A-B) and miR-96 (FIGS. 2C-D) in a Renilla/Firefly Luciferase reporter assay.

FIGS. 3A-H. Regulation of endogenous palladin levels in Hs578 cells (FIGS. 3A-E) and 4T1 cells (FIGS. 3F-H) over-expressing miR-96, miR-182 or a scrambled control sequence.

(FIG. 4A) Wound healing assay, Hs578 cells. Left panel—pictures (five fields) taken at the indicated time points following scratch. Right panel—percentage of open wound at each time point compared to time 0; (FIG. 4B) Matrigel invasion assay, Hs578 cells. Left panel—representative fields. Right panel—invasion rate relative to control; (FIG. 4C) Transwell migration assay, 4T1 cells. Left panel—representative fields. Right panel—migration rate relative to control; (FIG. 4D) Matrigel invasion assay, 4T1 cells. Left panel—representative fields. Right panel—invasion rate relative to control.

(FIG. 6A) Palladin mRNA expression level following stable over-expression of palladin shRNA (Palladin KD) or a scrambled shRNA (Ctrl) in 4T1 cells; (FIG. 6B) Palladin protein level following stable over-expression of palladin shRNA (Palladin KD) or a scrambled shRNA (Ctrl) in 4T1 cells; (FIG. 6C) Transwell migration assay and (FIG. 6D) Matrigel invasion assay in 4T1 cells stably expressing palladin shRNA (palladin KD cells) or a scrambled shRNA (Ctrl cells) and transfected with either miR-96, miR-182 or a scrambled control sequence (Ctrl). Left panels—representative fields, right panels—migration/invasion relative to control.

FIGS. 8A-D. MiR levels (FIGS. 8A-B) and palladin expression (FIGS. 8C-D) in primary tumors from mice injected with 4T1 cells stably transformed with miR-96, miR-182 or a scrambled RNA molecule.

(FIGS. 9A-C) Tumor volume, tumor diameter and mice weight starting from day 5 following inoculation of the tumor cells; (FIG. 9D) exemplary fluorescence measurements at the removal day of the tumors; (FIGS. 9E-F) average tumor area and average weight at the day of their removal.

FIGS. 10A-E. Lung metastasis in mice injected with 4T1 cells stably transformed with miR-96, miR-182 or a scrambled RNA molecule. (FIG. 10A) Exemplary CT photos of lungs. Metastatic nodules are marked with an arrow; (FIGS. 10B-C) Average quantity of lung metastatic nodules and average diameter of lung metastases; (FIGS. 10D-E) Exemplary fluorescence measurements in lungs and the average percentage of fluorescent area per lung. Metastatic areas are circled with white line.

DETAILED DESCRIPTION OF THE INVENTION

Figure 3D:
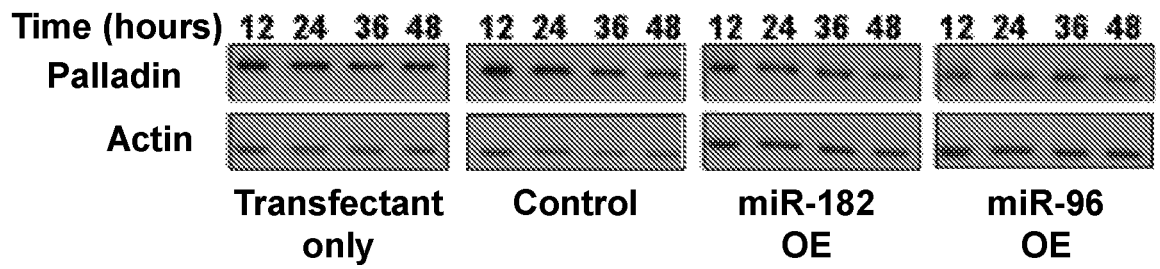
Figure 3E:
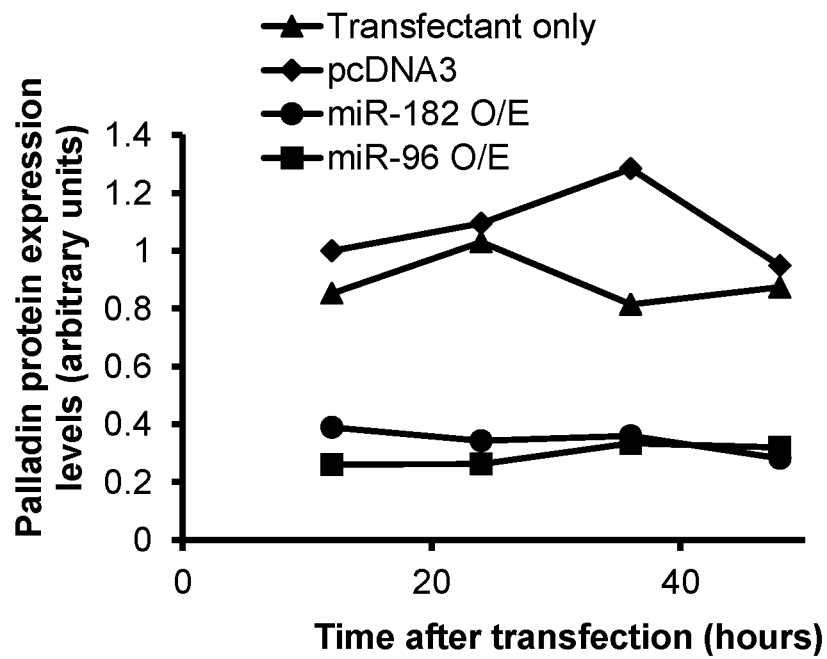

The present invention provides according to some aspects compositions and methods for treating cancer in a subject. More particularly, the compositions and methods of the present invention are particularly useful for inhibiting and even preventing cancer metastasis.

In some embodiments, the compositions and methods according to embodiments of the present invention utilize specific miRNAs, namely, human miR-96 (also termed hsa-miR-96) and/or human miR-182 (also termed hsa-miR-182). Such compositions and methods are particularly useful for treating cancer and cancer metastasis, as exemplified herein.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility is a separate embodiment. The terms further include oligonucleotides composed of naturally occurring bases, sugars, and covalent internucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

As used herein the term "vector" refers to recombinant constructs engineered to encode or express polynucleotides in a target cells, such as DNA, RNA, miRNA, shRNA, siRNA, antisense oligonucleotides, and the like. Vectors may include such vectors as, but not limited to, viral and non-viral vectors, plasmids, and the like.

As used herein, the term "expression vector" refers to a vector containing a nucleic acid sequence coding for at least part of a gene product capable of being expressed in a host cell. Expression vectors typically contain a variety of "control sequences," which refer to nucleic acid sequences necessary, for example, for the transcription of an operably linked coding or non-coding sequence in a particular host organism. In addition to control sequences, vectors and expression vectors may contain nucleic acid sequences that serve other functions as well. In some embodiments, an expression vector can be used to encode for or express one or more miRNA molecules in a target cell.

As referred to herein, the term "complementarity" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus cell, and the like. The cells may be selected from isolated cells, tissue cultured cells, cell lines, cells present within an organism tissue and body, and the like.

The term "treating" and "treatment" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include one or more of the following: a decrease in the rate of growth of the cancer (i.e. the cancer still grows but at a slower rate); cessation of growth of the cancerous growth, i.e., stasis of the tumor growth, and, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. In some embodiments, the cancer is a solid tumor. In some exemplary embodiments, the cancer is breast cancer.

As used herein, the terms "metastasis", "cancer metastasis" or "tumor metastasis" are used interchangeably and refer to the growth of cancerous cells derived from the primary cancerous tumor in another location or tissue. Metastasis also encompasses micrometastasis, which is the presence of an undetectable amount of cancerous cells in an organ or body part which is not directly connected to the organ of the original, primary cancerous tumor. Metastasis can also be defined as several steps of a process, such as the departure of cancer cells from an original tumor site, and migration and/or invasion of cancer cells to other parts of the body.

As used herein, "reducing or preventing cancer metastasis" refers to slowing or even completely inhibiting the formation, spread, development and/or growth of metastasis from the primary tumor. The term may also include reducing the number of metastases in an organ or tissue, as well as reducing the size and/or malignancy status of existing metastases.

The term "organism" refers to a mammal. In some embodiments, the organism is human. In some embodiments, the organism is selected from a pet, a rodent, a farm animal, and a lab animal.

As used herein the term "subject" is interchangeable with an individual or patient. According to some embodiments, the subject is a mammal. According to some embodiments, the subject is a human According to some embodiments, the subject is symptomatic. According to other embodiments, the subject is asymptomatic. In some embodiments, the subject is a human afflicted with cancer. In some embodiments, the subject is preferably an individual with the C allele of the polymorphic site within the PALLD gene identified by reference number rs1071738. In some embodiments, the subject is at risk of developing metastasis. In other embodiments, the subject has already developed metastases.

As used herein the term "small interfering RNA" and "siRNA" are used interchangeably and refer to a nucleic acid molecule mediating RNA interference or gene silencing. The siRNA inhibits expression of a target gene and provides effective gene knock-down.

The terms "microRNA" and "miRNA" are directed to a small non-coding RNA molecule that can function in transcriptional and post-transcriptional regulation of target gene expression. The terms encompasses a mature miRNA sequence or a precursor miRNA sequence, including a primary transcript (pri-miRNA) and a stem-loop precursor (pre-miRNA). The biogenesis of a miRNA initiates in the nucleus by RNA polymerase II transcription, generating a primary transcript (pri-miRNA). The primary transcript is cleaved by Drosha ribonuclease III enzyme to produce an approximately 70 nt stem-loop precursor miRNA (pre-miRNA). The pre-miRNA is then actively exported to the cytoplasm where it is cleaved by Dicer ribonuclease to form the mature miRNA. One strand of this miRNA is incorporated into an RNA-induced silencing complex (RISC) which recognizes target mRNAs through imperfect base pairing with the miRNA, and most commonly results in translational inhibition or destabilization of the target mRNA. Typically, the target mRNA contains a sequence complementary to a "seed" sequence of the miRNA, which usually corresponds to nucleotides 2-8 of the miRNA. The seed sequence is considered to be essential for the binding of the miRNA to the mRNA. Information concerning miRNAs and associated pri-miRNA and pre-miRNA sequences is available in miRNA databases such as miRBase (Griffiths-Jones et al. 2008 Nucl Acids Res 36, (Database Issue: D154-D158) and the NCBI human genome database.

The terms "miRNA molecules" and "miR molecules" refer to the miR-96 and/or miR-182 miRNA molecules. When referring to the miR molecules, the reference is to either one or both of said miRNA molecules. Each possibility being a separate embodiment.

The term "polynucleotides of the invention" refers to the miRNA molecules (i.e. miR-96 and/or miR-182) and/or to vectors expressing or encoding the same.

In some embodiments, the miRNA molecules may be modified at the base moiety, sugar moiety, or phosphate backbone, for example, in order to improve stability of the molecule, hybridization, transport into the cell, and the like. In addition, modifications can be made to reduce susceptibility to nuclease degradation. The miR molecules may have other appended groups such as peptides (for example, for targeting host cell receptors in vivo), or agents facilitating transport across the cell membrane or the blood-brain barrier, hybridization-triggered cleavage agents or intercalating agents. Various other well known modifications can be introduced as a means of increasing intracellular stability and half-life. Possible modifications include, but are not limited to, the addition of flanking sequences of ribo- or deoxy-nucleotides to the 5' and/or 3' ends of the molecule. In some circumstances where increased stability is desired, nucleic acids having modified internucleoside linkages such as 2'-O-methylation may be used. Nucleic acids containing modified internucleoside linkages may be synthesized using reagents and methods that are well known in the art.

The term "plurality" as used herein is directed to include more than one component.

As used herein, the term "about", when referring to a measurable value is meant to encompass variations of +/−10%, more preferably +/−5%, even more preferably +/−1%, and still more preferably +/−0.1% from the specified value.

According to some embodiments, there is provided a method for reducing or preventing cancer metastasis in a subject in need thereof, the method comprising administering to the subject at least one miRNA molecule selected from the group consisting of miR-96 and miR-182, or at least one vector expressing or encoding the same, thereby reducing or preventing cancer metastasis in the subject.

According to some embodiments, there is provided a method for reducing or preventing cancer metastasis cancer metastasis in a subject in need thereof, the method comprising administering to the subject miR-96 and/or miR-182, or a corresponding vector expressing or encoding the same, thereby reducing or preventing cancer metastasis in the subject.

According to some embodiments, there is provided a method of reducing or preventing cancer metastasis in a subject in need thereof, the method include inhibiting or reducing expression of palladin in the cancer cells and/or cancer metastasis cells. In some embodiments, reducing or inhibiting expression of palladin is achieved by administration of miR-96 and/or -miR-182 or one or more vectors encoding for said miRNA molecules. Each possibility is a separate embodiment.

According to some embodiments, there is provided a method for treating cancer in a subject in need thereof, the method comprising administering to the subject at least one miRNA molecule selected from the group consisting of miR-96 and miR-182, or at least one vector expressing or encoding the same, thereby treating cancer in the subject.

According to some embodiments, there is provided a method for treating cancer in a subject in need thereof, the method comprising administering to the subject miR-96 and/or miR-182, or a corresponding vector expressing or encoding the same, thereby treating cancer in the subject.

According to some embodiments, there is provided a method of treating cancer in a subject in need thereof, the method include inhibiting or reducing expression of palladin in the cancer cells. In some embodiments, reducing or inhibiting expression of palladin is achieved by administration of miR-96 and/or -miR-182 or one or more vectors encoding for said miRNA molecules. Each possibility is a separate embodiment.

In some embodiments, the methods may further include determining that the subject is carrying the C allele of the single nucleotide polymorphism (SNP) rs1071738 prior to administering the at least one miRNA molecule or the at least one vector expressing or encoding the same.

In some embodiments, the subject is at risk of developing metastasis and the administering is carried out prior to metastasis formation. In some embodiments, the subject has already developed metastases and the administering is carried out after metastasis formation.

In some embodiments, the cancer is a cancer associated with an abnormal palladin expression and/or activity.

According to some embodiments, there is provided a pharmaceutical composition comprising at least one miRNA molecule selected from the group consisting of miR-96 and miR-182, or at least one vector expressing or encoding the same, for use in reducing or preventing cancer metastasis.

According to some embodiments, there is provided a pharmaceutical composition comprising miR-96 and/or miR-182, or corresponding vector(s) expressing or encoding the same, for use in reducing or preventing cancer metastasis.

According to some embodiments, there is provided a pharmaceutical composition comprising at least one miRNA molecule selected from the group consisting of miR-96 and miR-182, or at least one vector expressing or encoding the same, for use in treating cancer.

According to some embodiments, there is provided a pharmaceutical composition comprising miR-96 and/or miR-182, or corresponding vector(s) expressing or encoding the same, for use in treating cancer.

According to some embodiments, there is provided a pharmaceutical composition comprising miR-96 and/or miR-182, or corresponding vector(s) expressing or encoding the same, for use in reducing palladin expression in cancer cells.

According to some embodiments, each of miR-96 and miR-182, or the corresponding vectors expressing or encoding the same are formulated in distinct compositions (such as pharmaceutical compositions), that may be administered concomitantly or separately.

According to some embodiments, both the miR-96 and the miR-182, or the corresponding vectors expressing or encoding the same are formulated in one composition (such as pharmaceutical composition).

In some embodiments, both the miR-96 and miR-182 are encoded or expressed by the same vector. In some embodiments, each of the miR-96 and the miR-182 are encoded or expressed by separate vectors.

In some embodiments, use of a composition and/or treatment according to the present invention is carried out through direct provision of miRNA. In other embodiments, treatment according to the present invention is carried out through introduction of an expression vector containing DNA encoding the miRNA. In other embodiments, treatment according to the present invention is carried out through introduction of a vector containing expressing the miRNA. The miRNA, or DNA sequence encoding the same, may include mature miRNA sequences, pri-miRNA sequences or pre-miRNA sequences. In some embodiments, use of dedicated delivery platforms may be utilized, for a specific and efficient delivery of the miRNA molecules to target cells and organs, in-vivo.

In some embodiments, a mature miR-96 comprises or consists of nucleotide sequence: UUUGGCACUAGCA-CAUUUUUGCU (SEQ ID NO: 1).

In some embodiments, an exemplary pri-miRNA of miR-96 comprises or consists of nucleotide sequence:

```
                                              (SEQ ID NO: 2)
ACUGUGAACAGUCUCAGUCAGUGAAUUACCGAAGGGCCAUAAACAGA

GCAGAGACAGAUCCACGAGGGCCUCCGGAGCACCUUACCCACUUCUGCCU

UGAGUGCUCCUAGACGUCGGAAACAGGCUGCUUCCAAGGGUGCAGGGAUG

CAAGGCCCCUCGUCCAGUGUGUCCCCAGAGAGCCCGCACCAGUGCCAUCU

GCUUGGCCGAUUUUGGCACUAGCACAUUUUUGCUUGUGUCUCUCCGCUCU

GAGCAAUCAUGUGCAGUGCCAAUAUGGGAAAAGCAGGACCCGCAGCUGCG

UCCGCCUCCCCUGCAUCCUUGUGUCAGGGCCCCAGCCUGCUCCUCCUCAA

GGCCUCCUCACCGCCUCCCCAGCCCAUCUGGCUCAGCUGCUGUGUGAGGG

CCCAGCGCUGGUGGGCAGCCAGAUCGCCUUACACUGCCUGGGGCCACGGU

AGAGCUGGGAGCCCAGCAAUCUGAGCUGGG
```

In some embodiments, an exemplary pre-miRNA of miR-96 comprises or consists of nucleotide sequence:

```
                                              (SEQ ID NO: 3)
UGGCCGAUUUUGGCACUAGCACAUUUUUGCUUGUGUCUCUCCGCUCUGA
GCAAUCAUGUGCAGUGCCAAUAUGGGAAA
```

In some embodiments, a mature miR-182 comprises or consists of nucleotide sequence: UUUGGCAAUGGUA-GAACUCACACU (SEQ ID NO: 4).

In some embodiments, an exemplary pri-miRNA of miR-182 comprises or consists of nucleotide sequence:

```
                                              (SEQ ID NO: 5)
GGAGAGGAGGGGGCUGAGGAGGGACCGGGACCAGCAGGAAGGGGGA

CUGUGGGGUUGGGCCUCCACACCAGGGCGACCCUGCAGGAAGGACCUUGU
```

-continued

CGCAGUUGCGGGAUGGGCGCCUCUGUCCUGGCCCUGCCUGGACCAUCCU

AACUGUCUCUGUCUCUUCCUCAGCACAGACCGAGGCCUCCCCAGCUCCUG

GGGGGAGCUGCUUGCCUCCCCCCGUUUUUGGCAAUGGUAGAACUCACACU

GGUGGGUAACAGGAUCCGGUGGUUCUAGACUUGCCAACUAUGGGGCGAGG

ACUCAGCCGGCACCCUGUGCACAGCCAGCGAGGGAAGGGCCGGCCAUGCU

GGACCGCUGUUCUCCGCGAGGAAGGAGGGGACUCAGGUCCCGGACUGCUG

GGUAGUGGCAGAGGGCAGGUGCAGCUGGAAGUGACACUCUGUGUUUCCCU

GCAUCCCCCUGAGGUCACAGGUCCUCAAGUCAGCUGGGAAGCCGUUCUCU

GGCCCUCAGGGG.

In some embodiments, an exemplary pre-miRNA of miR-182 comprises or consists of nucleotide sequence:

(SEQ ID NO: 6)
GAGCUGCUUGCCUCCCCCCGUUUUUGGCAAUGGUAGAACUCACACUG
GUGAGGUAACAGGAUCCGGUGGUUCUAGACUUGCCAACUAUGGGGCGAG
GACUCAGCCGGCAC.

The above sequences are RNA sequences containing U nucleotides. It is to be understood that when expression vectors are used, containing DNA sequences encoding the RNA, T nucleotides should be provided.

In some embodiments, analogues of the miRNA sequences provided herein may be used, as long as they maintain the ability to regulate their target. "Analogs" herein encompass miRNA sequences of the present invention in which one or more bases are substituted or deleted. Preferably, in order to maintain the activity towards the target mRNA, the "seed" sequence, which is a sequence completely complementary to a sequence within the mRNA targeted by the miR and thus essential for the binding, should remain unchanged. The seed sequence corresponds to positions 2-7 of the miR. In some embodiments, for example in cases where the palladin gene contains a mutation in the region recognized by the seed sequence, the miR molecule may be designed to match the mutated sequence. For example, the miR may be designed with a nucleotide matching the mutated one on the target sequence, i.e., a nucleotide complementary to the mutated one.

In some embodiments, an analogue has at least about 75% identity or complementarity to a sequence of the invention, for example at least about 80%, at least about 85%, at least about 90%, at least about 99% identity or complementarity to a sequence of the invention. Each possibility represents a separate embodiment of the present invention.

In some embodiments, the miR molecules may be introduced to a cell, a tissue or an organism by any of the methods known in the art. In some embodiments, the miR molecules may be introduced in the form of a composition (one composition or separate compositions). In some embodiments, the composition is a pharmaceutical composition, comprising one or more suitable excipients. In some embodiments, the miR molecules may be expressed or encoded in a target cell, tissue or organism by an exogenous vector introduced thereto. In some embodiments, the vector may be comprised in a composition. In some embodiments, the vector may be introduced to a cell, tissue or organism by any of the methods known in the art. In some exemplary embodiments, the miRNA molecules may be introduced in the form of a single strand RNA molecule (ssRNA), double strand RNA molecule (dsRNA), or an RNA molecule which is at least partially double stranded. Each possibility is a separate embodiment. In some embodiments, the vector miRNA molecules may be encoded by one vector. In some embodiments, the miRNA molecules may be encoded by separate vectors.

In some embodiments, the miR-96 and the miR-182 may be encoded by a single vector. In some embodiments, the miR-96 and the miR-182 may each be encoded by a separate vector. In some embodiments, the miR-96 and the miR-182 may be formulated in the same composition or in separate compositions.

In some embodiments, the miR-molecules may be introduced or expressed or encoded in a cell, tissue or organism in combination with one or more additional reagent. In some embodiments, the additional reagent may be a therapeutic reagent (drug). In some embodiments, the additional reagent may include other polynucleotide molecule(s). In some embodiments, the miR-molecules (or vector(s) encoding or expressing the same) and the additional reagent may be administered in the same or different composition and they may be administered simultaneously, or sequentially, at any time interval.

In some embodiments, the miRNA molecules or vectors encoding the same may be administered systemically (enterally or parenterally) or locally, for example via intra-tumor injection. Each possibility represents a separate embodiment of the present invention.

In some embodiments, administration is systemic administration. In other embodiments, the administration is localized administration. In some embodiments, localized administration is into a tumor. In additional embodiments, localized administration is into a space or cavity adjacent to a tumor. In other embodiments, localized administration is into a space or cavity formed after tumor resection.

Non-limiting examples of suitable administration routes include intravenous, intramuscular, subcutaneous, transdermal, intradermal and oral administration. Each possibility represents a separate embodiment of the present invention.

In some embodiments, miRNA molecules or expression vectors are injected into a space adjacent to a tumor. In other embodiments, they are injected into a space formed following excision of the tumor.

In some embodiments, for example when miRNA molecules or expression vectors are administered systemically, targeting moieties may be used. Targeting the nucleic acid constructs to a particular cell can be performed by any method known to those skilled in the art. For example, the construct can be conjugated to an antibody that recognizes cell surface antigens unique to cancer cells, or that are more prevalent on cancer cells, compared to normal cells. As another example, the construct can be conjugated to a ligand specifically recognized by receptors unique to cancer cells, or that are more prevalent on cancer cells.

According to some embodiments, various delivery systems are known and can be used to transfer/introduce the polynucleotides and/or composition of the invention into cells, such as, for example, encapsulation in liposomes, targeted liposomes, dendtritic polyglycerolamine nanocarriers, nanoparticles, microparticle s, microcapsules, electroporation, nucleofection, ultrasound based, laser based, recombinant cells that are capable of expressing the composition, receptor-mediated endocytosis, construction of the composition of the invention as part of a viral vector or other vector, viral vectors that are capable of being reproduced without killing the cell during the process of reproduction and that comprise the composition of the invention, viral vectors that are not capable of reproduction and that comprise the composition of the invention, injection of cells that produce viral vectors that comprise the composition of the invention, injection of polynucleotides, electroporation, calcium phosphate mediated transfection, and the like, or any other methods known in the art or to be developed in the future.

In some embodiments, the polynucleotide and compositions of the invention may be suitably formulated for intravenous, intramuscular, subcutaneous, intracervical, intratumoral, or intraperitoneal administration.

In some embodiments, the polynucleotide and compositions described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

In some embodiments, where the target cells are in vivo, the polynucleotides and composition of the invention can be administered by any convenient protocol. In some embodiments, the protocol employed is a nucleic acid administration protocol, where a number of different such protocols are known in the art. For example, the nucleic acids may be introduced into tissues or host cells by any number of routes, including viral infection, microinjection, fusion of vesicles, or Jet injection for intramuscular administration. In some embodiments, the nucleic acids may be coated onto gold microparticles, and delivered intradermally by a particle bombardment device. In some embodiments, expression vectors may be used to introduce the nucleic acids into a cell. In some embodiments, the polynucleotides or compositions of the invention may be fed directly to, injected into, the host organism containing a desired target gene. In some embodiments, the polynucleotides or compositions of the invention may be directly introduced into the cell (i.e., intracellularly); or introduced extracellularly into a cavity, interstitial space, into the circulation of an organism, introduced orally, and the like. Methods for oral introduction include direct mixing of a polynucleotide (such as, RNA) with food of the organism. Physical methods of introducing polynucleotides include injection directly into the cell or extracellular injection into the organism of a polynucleotide solution (composition), such as, an RNA solution. The polynucleotides of the invention may be introduced in an amount which allows delivery of at least one copy per cell. Higher doses (for example, at least 5, 10, 100, 500 or 1000 copies per cell) of the polynucleotide may yield an enhanced effect, whereas lower doses may be useful for specific applications. In some embodiments, a hydrodynamic nucleic acid administration protocol may be used. In some embodiments, the polynucleotides of the invention can be incorporated into a variety of formulations (compositions) for therapeutic administration. More particularly, the polynucleotides of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, intratumoral, intracervical, intra-tissue and the like, administration. In pharmaceutical dosage forms, the polynucleotides may be administered alone or in appropriate association, as well as in combination, with other pharmaceutically active compounds. In some embodiments, the pharmaceutical dosage forms, may be administered locally, by being disposed or contained in a device.

In some embodiments, use of dedicated delivery platforms may be utilized, for a specific and efficient delivery of the miRNA molecules to target cells and organs, in-vivo.

According to some embodiments, any suitable devilry vehicle may be used to deliver the polynucleotides of the invention to target cell, tissue or organ (such as cancer cell and/or metastases). In some embodiments, the delivery is specific, efficient and targeted, such that non-target cells, tissues or organs are not affected.

According to some embodiments, nanocarriers may be used to deliver the polynucleotides of the invention. In some exemplary embodiments, the nanocarriers may include dendritic polyglycerolamine (dPG-NH2). dPG-NH2 is a cationic hyperbranched polymer, that can improve miRNA and siRNA stability, intracellular trafficking, silencing efficacy, and accumulation in the tumor environment due to the enhanced permeability and retention effect. dPG-NH2 exhibited low cytotoxicity and high efficacy in delivering active siRNA/miRNA into cells.

According to some embodiments, liposomal particles, such as, targeted liposomes may be used to deliver the polynucleotides of the invention. In some exemplary embodiments, targeted liposomes, that can deliver polynucleotide molecules (such as, miRNAs) may be targeted using an appropriate targeting moiety, such as antibodies targeting specific cancer cells, for example, based on receptors present on these cells. In some embodiments, the particles may be coated with glycosaminoglycan (such as, hyaluronan).

According to some embodiments, nanoparticles, coupled to pentapeptide may be used to deliver the polynucleotides of the invention. In some exemplary embodiments, the pentapeptide coupled carriers utilize the pentapeptide Tyr-Ile-Gly-Ser-Arg (YIGSR) (SEQ ID NO: 17), that can enhance specific binding to cancer cells and cancer metastatic cells, thereby efficiently and specifically deliver the polynucleotides of the invention to target cells, tissues and organs.

In some embodiments, in determining the dosages of the compositions to be administered, the dosage and frequency of administration may be selected in relation to the pharmacological properties of the nucleic acids to be delivered (i.e., naked RNA, vectors, delivery particles used, and the like). In some embodiments, the miR molecules (alone or in combination with other agents) may be administered in a dose having an amount of between about 0.01 mg and about 10 mg per administration/treatment per day/per miRNA molecules. For example, the amount may be between about 0.01 mg and about 8 mg per administration/treatment. For example, the amount may be between about 0.01 mg and about 2 mg per administration/treatment. For example, the amount may be between about 0.05 mg and about 4 mg per administration/treatment. For example, the amount may be between about 0.05 mg and about 2 mg per administration/treatment. For example, the amount may be between about 0.08 mg and about 2 mg per administration/treatment. For example, the amount may be between about 0.08 mg and about 1 mg per administration/treatment. For example, the amount may be between about 0.5 mg and about 9 mg per administration/treatment. In some exemplary embodiments, the miR molecules may be formulated in a saline solution (such as PBS). In some embodiments, the doses disclosed herein may be administered at any administration regime, such as, 1-5 times a day; 1-10 times a week, 1-15 times a month, and the like, at identical or different time intervals and/or at the same or different time of day.

In some embodiments, for oral preparations, the polynucleotides can be used alone or in combination with appropriate additives to make tablets, powders, granules or capsules, for example, with conventional additives, such as lactose, mannitol, polyglutamic acid (PLGA) poly lysine acid (PLA), corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In some embodiments, the polynucleotides can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, the pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public. Those of skill in the art will readily appreciate that dose levels can vary as a function of the specific compound, the nature of the delivery vehicle, and the like. Preferred dosages for a given compound are readily determinable by those of skill in the art by a variety of means.

In some embodiments, the compositions of the invention may be advantageously combined and/or used in combination and/or alternation with other agents which are either therapeutic or prophylactic agents, and different from the subject compounds. The compositions may also be advantageously combined and/or used in combination with agents that treat conditions often associated with the treated condition. In certain embodiments, administration in conjunction with the subject compositions enhances the efficacy of such agents. In some embodiments, the therapeutic agents may include chemotherapeutic agents, such as, Alkylating agents, Anthracyclines, Cytoskeletal disruptors Taxanes), Epothilones, Histone Deacetylase Inhibitors, Inhibitors of Topoisomerase I, Inhibitors of Topoisomerase II, Kinase inhibitors, Nucleotide analogs and precursor analogs, Peptide antibiotics, Platinum-based agents, Retinoids, *Vinca* alkaloids and derivatives, and the like, or combinations thereof. Each possibility is a separate embodiment.

According to these embodiments, the delivery vehicle of the nucleic acid constructs comprises a targeting moiety or a mechanism for selective activity within the cancer cells only.

In some embodiments, cancers that can be treated by the compositions and methods disclosed herein include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma. Each possibility is a separate embodiment.

According to certain embodiments, the cancer is selected from cervical cancer, hepatic cancer, prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer. Each possibility is a separate embodiment.

In some embodiments, the cancers to be treated by the compositions and methods of the present invention are solid tumors, preferably solid tumors in which abnormal palladin activity and/or expression is associated with their pathogenesis, e.g., promotes invasiveness of the cancer. Such cancers include, e.g., cancers in which palladin is over-expressed and/or mutated. In some embodiments, the cancer is selected from the group consisting of breast cancer, pancreatic cancer and colorectal cancer. Each possibility represents a separate embodiment of the present invention. In some particular embodiments, the cancer is breast cancer.

According to some embodiments, reduction or prevention of metastasis development can be measured by standard methodologies known in the art including a reduction in size or numbers of tumors as measured by a variety of radiographic, imaging, circulating tumor marker, palpitation, direct measurement or observation techniques known in the art. Accordingly a reduction or prevention of metastasis development can also be measured by a reduction of a sign or symptom associated with the disease state of the cancer being treated or a prolongation of survival or reduction in suffering from a disease sign or symptom of the cancer being treated.

According to some embodiments, reagents and kits thereof for practicing one or more of the above-described methods are provided. The subject reagents and kits thereof may vary greatly. Typically, the kits at least include mir-96 and/or miR-182 molecule or vector(s) encoding or expressing the same, as described above. The kits may also include a pharmaceutically acceptable delivery vehicle, which may be combined with or separate from the miR-molecules in the kit. In addition to those components, the kits further include instructions for practicing the subject methods.

According to yet another aspect of the invention, there is provided a kit comprising the pharmaceutical composition, essentially as described above, and instructions for use of the kit.

In some embodiments, when treating cancer, administration of the nucleic acids of the invention (i.e., miRNA molecules or vectors(s) encoding or expressing the same), may be performed in combination with one or more additional treatments. For example, such combination therapy may be used to increase tumor susceptibility to chemotherapy and/or irradiation.

In some embodiments, when treating a cancer, repeated administration of the nucleic acids of the invention may be performed, wherein the dosages administered and the composition of the nucleic acid may be identical, similar or different. In some embodiments, the administration may be prolong (such as over the course of 1-120 hours).

The term comprising includes the term consisting of.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1—Regulation of Palladin by miR-96 and miR-182 in a Reporter Assay

The micro-RNAs ("miRs") miR-96 and miR-182 were identified as potential regulators of palladin protein expression in humans. To test regulation of palladin expression by miR-96 and miR-182, the sequence of the target area of these two miRs within PALLD, the gene encoding palladin in humans, was cloned and tested in a Lucieferase reporter assay, as follows:

Fragments of the 3' UTR of PALLD spanning the miRNA binding sites were cloned downstream to the *Renilla* Luciferase Reporter of the psiCHECK™-2 plasmid (Promega) that contains a Firefly Luciferase Reporter (used as control) under a different promoter. The PALLD gene has a known G/C polymorphism within the binding site of miR-96 and miR-182 (refSNP-rs1071738, see dbSNP website). In order to test the effect of this polymorphism on the regulation by the miRs, three *Renilla*/Firefly Luciferase psiCHECK2 constructs were generated for the reporter assay, as shown in FIG. 1. The sequences of human miR-96 (SEQ ID NO: 1) and miR-182 (SEQ ID NO:4) are shown aligned with their binding site within PALLD. "PALLD-G" (SEQ ID NO:15) and "PALLD-C" (SEQ ID NO:16) indicates a G or C nucleotide at the polymorphic position, respectively. "PALLD-TarDel" (SEQ ID NO:17) is a negative control construct lacking the binding site of the miRs (target deletion).

Pre-miRNAs (human miR-182 and miR-96) were cloned into the miRNA expression vector miRVec. HEK-293T or HeLa cells were co-transfected with the psiCHECK™-2 containing the desired 3' UTR and miRVec containing the desired pre-miRNA. 48 h after transfection, Firefly and *Renilla* Luciferase activities were measured using the Dual-Luciferase Reporter Assay System kit (Promega) and a Veritas microplate luminometer.

The results of the assay are shown in FIGS. 2A-D. Luciferase activity was significantly lower for the PALLD-C construct compared to the control construct, whereas no effect was seen for the PALLD-G construct, which showed Luciferase activity comparable to that of the control. These results demonstrate direct regulation of palladin by miR-96 and miR-182, which depends on the presence of C at the polymorphic position within the binding site of the miRs.

Example 2—Levels of Endogenous Palladin in Cells Over-Expressing miR-96/miR-182

The ability of miR-96 and miR-182 to inhibit palladin expression was further tested by measuring endogenous levels of palladin mRNA and protein in Hs578 cells (human mammary carcinoma) transfected with either miR-96 or miR-182 (expressed from miRvec plasmid as mentioned above). The Hs578 cells are heterozygote in the polymorphic position within the binding site of the miRs, having one C allele and one G allele.

Hs578 cells were transfected when cells were 60-75% Confluent. DNA plasmids were transfected together with a transfection reagent (lipofectamin 2000, Invitrogen) in Optimem serum (Biological Industries). GFP was transfected as a control and its detection was confirmed 24 hrs after transfection. 24 hrs following transfection the cells were harvested for RNA and protein extractions.

Measuring mRNA and miRNA levels: Total RNA was extracted using TRIzol reagent (Invitrogen, Life Technologies) and RNA quality was measured using a NanoDrop (Thermo Scientific). cDNA for miRNA and mRNA was synthesized from total RNA. Reverse transcription reaction for mRNA was carried out using random-primer and SuperScript III reverse transcriptase (Invitrogen). Reverse transcription reaction for specific miRNA was done using Taq-Man miRNA Assays (Applied Biosystems; ABI). Single miRNAs/mRNAs expression were tested similarly using TaqMan Universal PCR Master Mix (No AmpErase UNG; Applied Biosystems) or SYBR green PCR master mix (Applied Biosystems), respectively, using Step-One Sequence Detection System. Expression values were calculated based on the comparative threshold cycle (Ct) method. MiRNAs levels were normalized to U6 and mRNA expression levels were normalized to GAPDH.

Measuring protein levels: Hs578 cells were homogenized with a lysis buffer. Protein levels in the lysates were determined by using the Bio-Rad protein assay (Bio-Rad). Lysates were resolved by SDS-PAGE through 4-12% gels (GeBaGel, Gene Bio-Application) and transferred by electroporation to nitrocellulose membranes. Membranes were blotted with anti-palladin (Protein Group) or anti-actin (Millipore) antibodies, followed by a secondary antibody linked to horseradish peroxidase. Band quantification was performed using ImageJ software (National Institutes of Health).

The results are summarized in FIGS. 3A-E. Over-expression of either miR-96 or miR-182 significantly reduced endogenous levels of palladin protein.

In a further experiment, 4T1 cells (mice mammary carcinoma) which are homozygote to the C allele in the miRs' binding site were stably transformed with mouse miR-96 ("mmu-miR-96"), mouse miR-182 ("mmu-miR-182") or a scrambled sequence, and the levels of palladin protein were measured.

Generation of clones for transformation: A CD515B plasmid expressing the scrambled sequence under a CMV promoter was used as a control. Pre-miR-182 and pre-miR-96 of mice were amplified by PCR (using 4T1 cells' DNA as template) and each cloned into a CD515B plasmid, under the CMV promoter. The sequences of the three plasmids, following the CMV promoter, are:

Scrambled CD515B plasmid (SEQ ID NO: 7):
gacctccatagaagattctagagctagcgaattcGTGGTCCTCTCCGTGCTACCGCACTGTGGGTA

CTTGCTGCTCCAGCAGGGCACGCACAGCGTCCGTGGAGGGAAAGGCCTTTTCC

CCACTTCTTAACCTTCACTGAGAGGGTGGTTGGGGTCTGTTTCACTCCATGTGT

CCTAGATCCTGTGCTACAGACCTTCCTTTCTGTCCTCCCGTCTTGGACCTCAGT

CCTGGGGGCTCCAAAGTGCTGTTCGTGCAGGTAGTGTGATTACCCAACCTACT

GCTGAGCTAGCACTTCCCGAGCCCCGGGACACGTTCTCTCTGCCAATTGTCTT

CTTGGCTGAGCTCCCCAAGCTCCATCTGTCATGCTGGGGAGCCCAGTGGCGTT

CAAAAGGGTCTGGTCTCCCTCACAGGACAGCTGAACTCCGGGACTGGCCAGTG

TTGAGAGGCGGAGACTTGGNAAATTGCTGGACGCTgcggccgcaaggatctgcgatcgctcc ggtgccc mmu-miR-182 CD515B plasmid (SEQ ID NO: 8):
gacctccatagaagattctagactagcgaattcCTCCTAAAACCACCCTAACTGCTTCTTCTTCA

GCATAGGCTTACTGGTCTGGCTGCTGGAGGCCTCCCACCATTTTTGGCAATGG

TAGAACTCACACCGGTAAGGTAATGGGACCCGGTGGTTCTAGACTTGCCAAC

TATGGTGTAAGTGCTGAGCTGCTGAAGGTCTGCACCGTGCCGGAACCTGCCGA

TCACCAGGAAGGAGAGGGGACTCCTGTCTCCAGACCACCAGGCAGTgcggccgca aggatctgcgatcgctccggtgccc mmu-miR-182 mature sequence:
(SEQ ID NO: 9)
TTTGGCAATGGTAGAACTCACACCG

Stem-loop :
(SEQ ID NO: 10)
ACCATTTTTGGCAATGGTAGAACTCACACCGGTAAGGTAATGGGACCCGGT
GGTTCTAGACTTGCCAACTATGGT mmu-miR-96 CD515B plasmid (SEQ ID NO: 11):
gacctccatagaagattctagagctagcgaattcGGTGCCAGGGTACAAAGACCTCCTCTGCTCCT

TCCCCAGAGGGCCTGTTCCAGTACCATCTGCTTGGCCGAT*TTTGGCACTAGCAC*

*ATTTTGCT*TGTGTCTCTCCGCTGTGAGCAATCATGTGTAGTGCCAATATGGGA

AAAGCGGGCTGCTGCGGCCACGTTCACCTCCCCCGGCATCCCAGGGTCTGTGT

GTCTCACTGGCTCCCTGGCCCATCTGGCTTACTGCTGGGTGAGGAGGGTACAG

CCgcggcgcaaggatctgcgatcgctccggtgccc mmu-miR-96 mature sequence:
(SEQ ID NO: 12)
*TTTGGCACTAGCACATTTTTGCT*

Stem-loop:
(SEQ ID NO: 13)
CCAGTACCATCTGCTTGGCCGAT*TTTGGCACTAGCACATTTTTGCT*TGTGTCTCT
CCGCTGTGAGCAATCATGTGTAGTGCCAATATGGGAAAAGCGGGCTGCTGC The plasmid sequences are shown in lowercase letters and sequences of the cloned constructs are shown in uppercase letters. Sequences marked in boldface correspond to the recognition site of the restriction enzyme XbaI; underlined sequences correspond to the recognition site of NheI; sequences shown in italics correspond to the recognition site of EcoRI; sequences marked in boldface and underlined correspond to the recognition site of NotI.

Retroviral particles were prepared using HEK-293 cells that were co-transfected with CD515B plasmids and lentiviral vector packaging (Tarom) using PEI transfection reagent (sigma). Forty-eight hours following transfection retroviral particles were collected. For infection, the retroviral particles containing medium was added to 4T1 cells at 50% confluence in 6 wells plates. 48 hour later, Hygromycin (200 ug/ml, Sigma) was added to the medium for selection.

The results are summarized in FIGS. 3F-H. Over-expression of miR-96 or miR-182, but not the scrambled sequence, significantly reduced endogenous levels of palladin protein.

Example 3—Migration and Invasion of Cells Over-Expressing miR-96/miR-182

The effect of over-expression of miR-96 or miR-182 on cell migration and invasion was tested in Hs578 and 4T1 cells.

Hs578 Cells

Figure 4A:
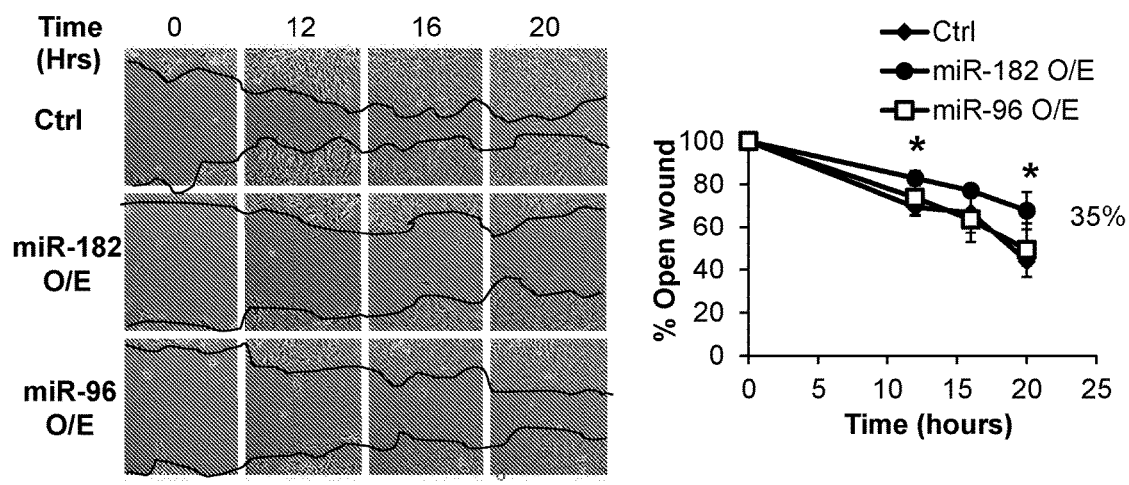
FIGS. 4A-D. Migration and invasion of cells over-expressing miR-96, miR-182 or a scrambled control sequence.

Migration—wound healing assay: Hs578 cells were plated in 12-well plates, transfected as indicated, and cultured to confluency. Cells were serum-starved for 8 h and scraped with a P200 tip (time 0). The percentage of open wound was assessed from pictures (five fields) taken at the indicated time points, using ImageJ software. The results are shown in FIG. 4A.

Figure 4B:
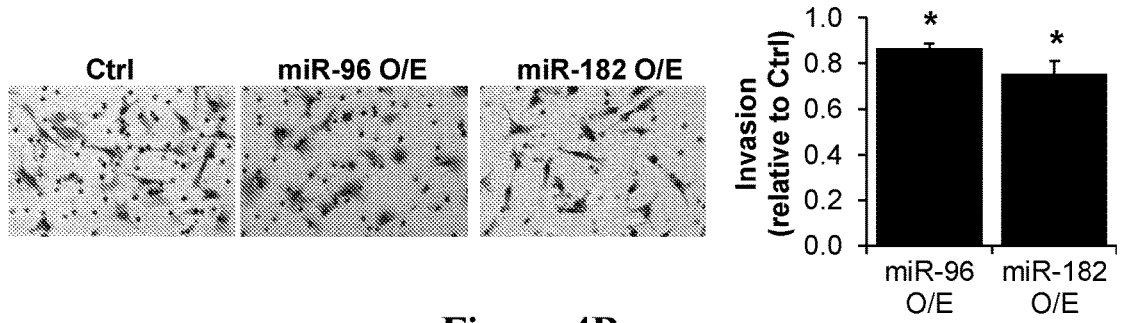

Invasion—Matrigel invasion assay: The invasive potential was assessed using Matrigel invasion chambers (BD Biosciences). One chamber consists of a cell insert and a well. The bottom of the cell insert is covered with a filter containing multiple 8-mm pores and is coated with a basement membrane matrix (Matrigel). Hs578 transfected cells were serum starved 0/N (starvation started 24 h following transfection for Hs578), harvested and re-suspended in serum free medium. Hs578 ($5*10^4$) were plated in serum-free medium in transwell inserts. Complete medium served as chemo-attractant in the lower chamber. After 20 h of incubation at 37° C. and 5% $CO_2$, the non-migrating cells present on the upper surface of the transwell were removed using a sterile cotton swab. The cells that were able to invade through the Matrigel and migrate onto the lower surface of the filter were fixed and stained with Diff-Quick (American Scientific Products, McGraw Park, Ill., USA). Filters were photographed and percentage of covered area was assessed using ImageJ software. Results were calculated as invasion rate in relation to control cells. Each experiment was repeated at least three times independently. The results are shown in FIG. 4B.

4T1 Cells

Figure 4C:
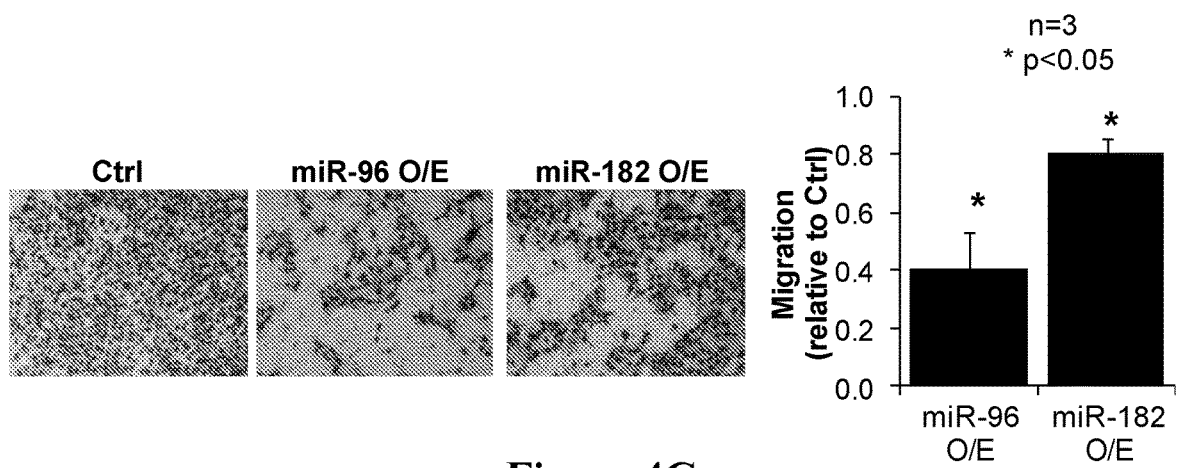
Figure 4D:
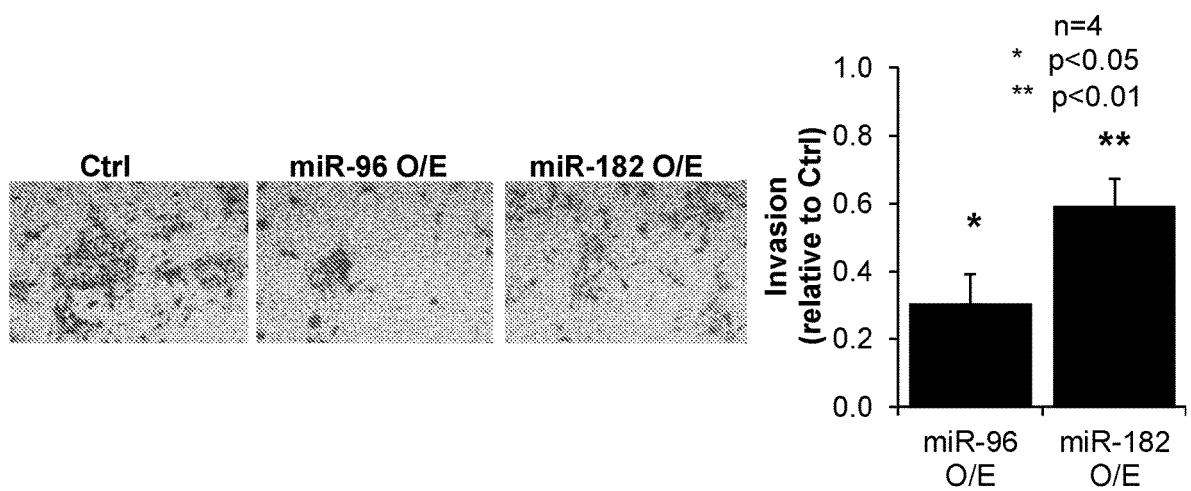

Transwell migration assay and Matrigel invasion assay were carried out as described above. The results are shown in FIG. 4C (transwell assay) and FIG. 4D (Matrigel assay).

As can be seen from the figures, over-expression of miR-96 or miR-182 resulted in a significant reduction of cell migration and invasion compared to the control scrambled sequence.

Example 4—Down-Regulation of miR-96/miR-182 and Effect on Palladin mRNA Levels

The effect of down-regulation of miR-96 or miR-182 on the mRNA levels of palladin, and cell migration was tested in MCF7 cells (human mammary carcinoma) transfected with an anti-miR-96, an anti-miR-182 or a scrambled sequence.

MCF7 cells were transfected when cells were 60-75% Confluent. Anti-miR miRNA inhibitors (Ambion (cat # AM17000)) for hsa-miR-182 and hsa-miR-96 or a scrambled sequence (mirVana™ miRNA Inhibitor, Negative Control #1, Cat. number: 4464076) were transfected together with a transfection reagent (lipofectamin 2000, Invitrogen) in Optimem serum (Biological Industries). GFP was transfected as control and its detection was confirmed 24 hrs after transfection. 24 hrs following transfection the cells were harvested for RNA extraction.

Figure 5A:
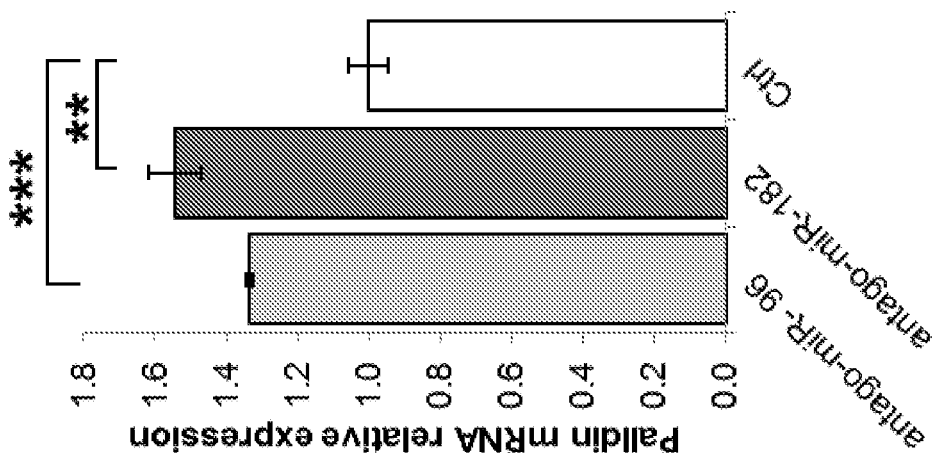
FIGS. 5A-F. Effect of down-regulation of miR-96 or miR-182 on the mRNA levels of palladin (FIGS. 5A-C) and cell migration (FIG. 5D) in MCF7 cells; and on cell migration (FIG. 5E) and invasion (FIG. 5F) in 4T1 cells. Ctrl-scrambled control sequences; Standard errors are shown in FIGS. 5A-C.
Figure 5B:
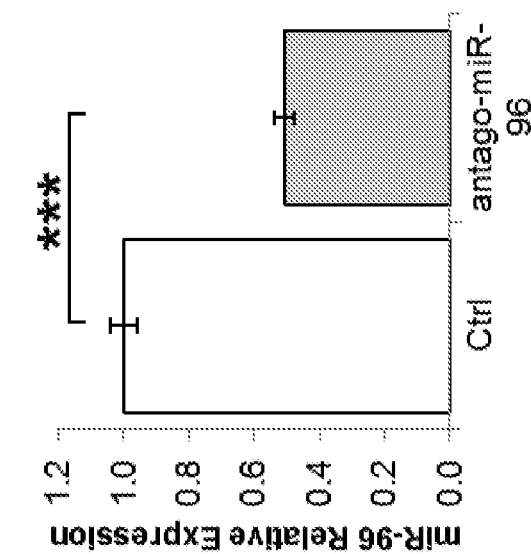
Figure 5C:
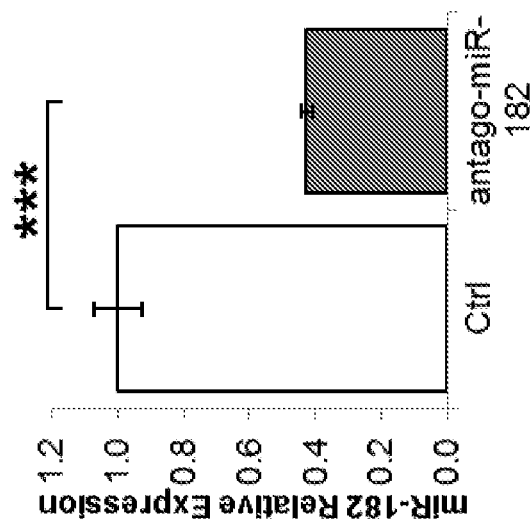

As shown in FIGS. 5A-B, transfection with the anti-miR miRNA inhibitors reduced the endogenous expression levels of the respective miRs. The levels of palladin mRNA was increased in the cells in which miR-96 or mi-182 were down-regulated compared to control cells transfected with the scrambled (CTRL) sequence (FIG. 5C).

Figure 5D:
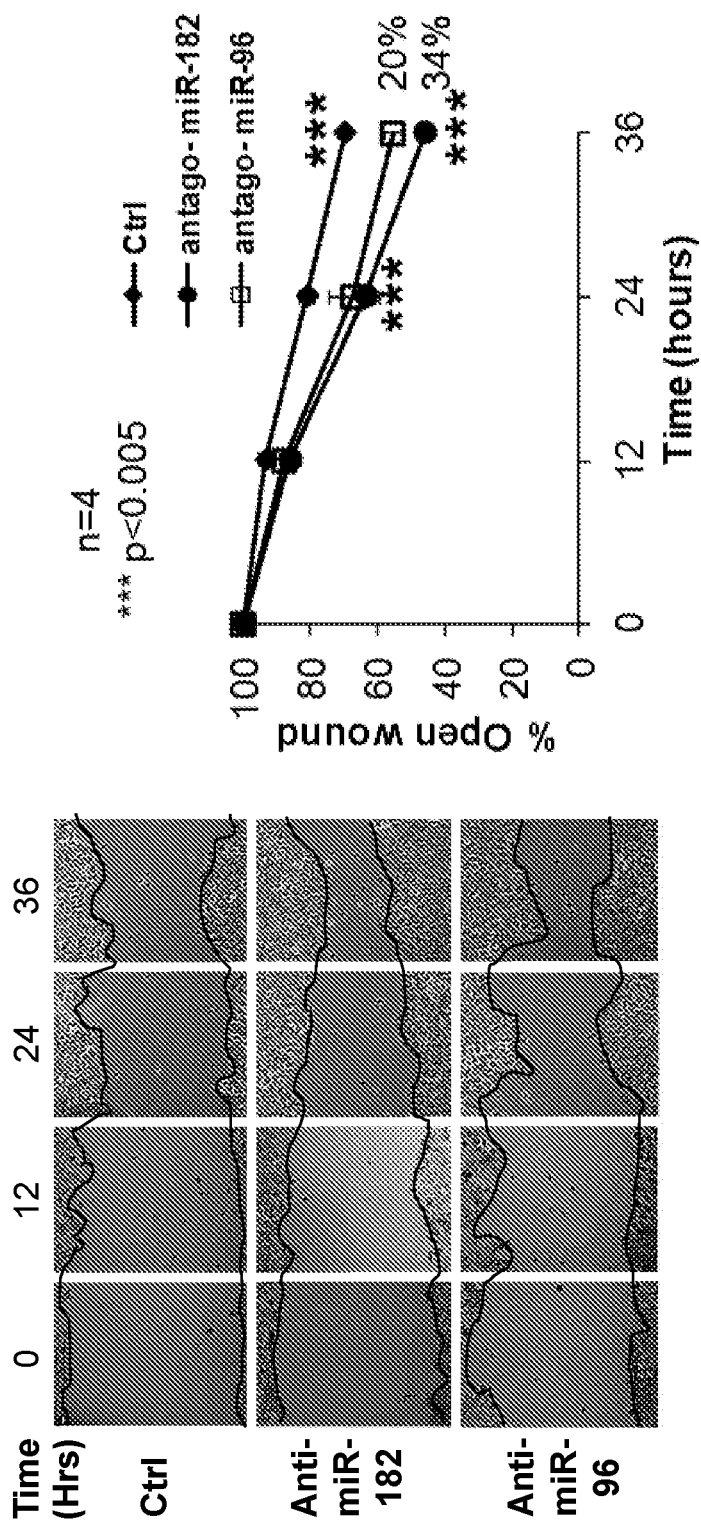

Migration—wound healing assay: MCF7 cells were plated in 12-well plates, transfected as indicated, and cultured to confluency. Cells were serum-starved for 8 h and scraped with a P200 tip (time 0). The percentage of open wound was assessed from pictures (five fields) taken at the indicated time points, using ImageJ software. The results are summarized in FIG. 5D (left panel—pictures taken at the indicated time points following scrape; right panel—percentage of open wound at each time point compared to time 0). Down-regulation of miR-96 or miR-182 resulted in increased cell migration.

The effect of down-regulation of miR-96 or miR-182 on cell migration and invasion was also tested in 4T1 cells transfected with an anti-miR-96, an anti-miR-182 or a scrambled sequence using Transwell migration assay and Matrigel invasion assay.

Figure 5E:
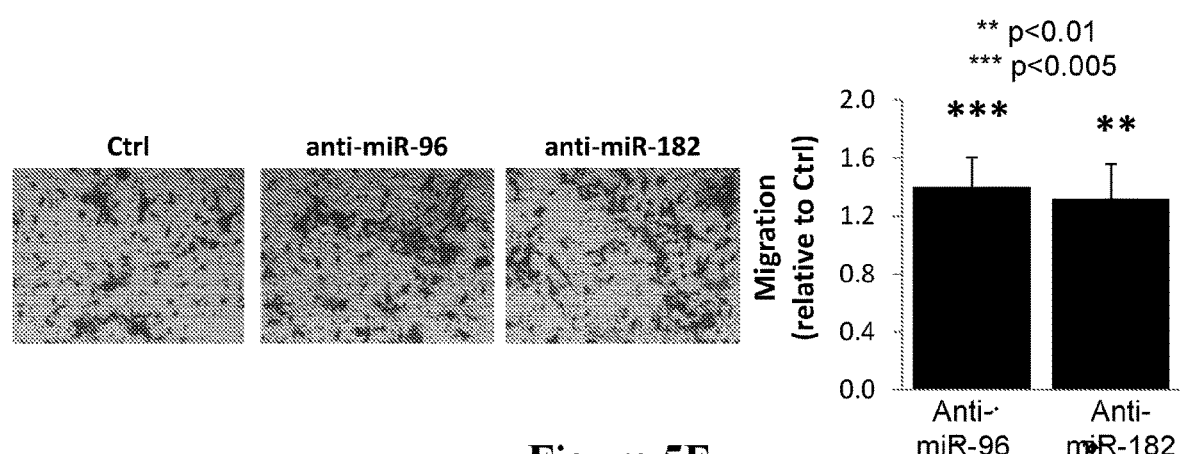
Figure 5F:
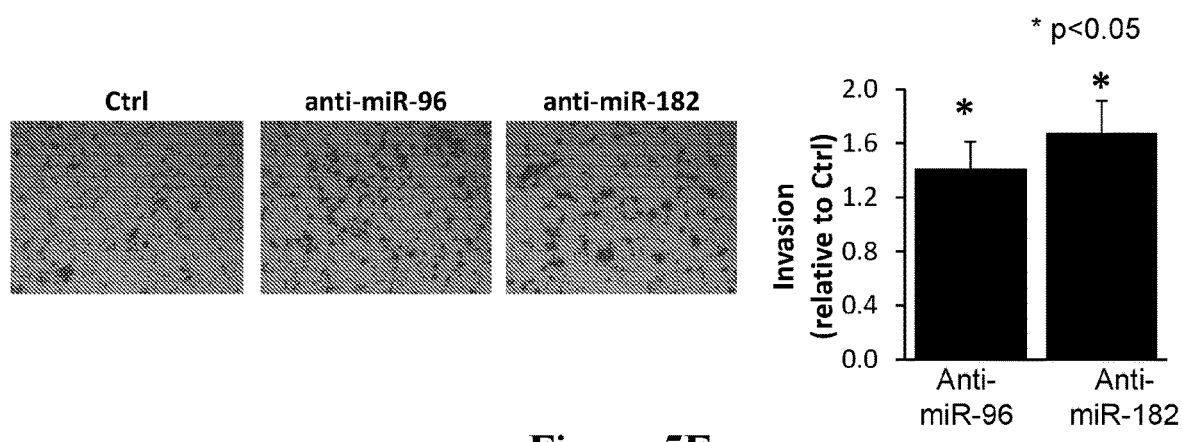

The results are summarized in FIGS. 5E-F (left panels—representative fields; right panels—migration/invasion rate relative to control). Down-regulation of miR-96 or miR-182 by anti-miR transfection enhanced migration and invasion of the 4T1 cells.

Example 5—Down-Regulation of Palladin mRNA

Figure 6A:
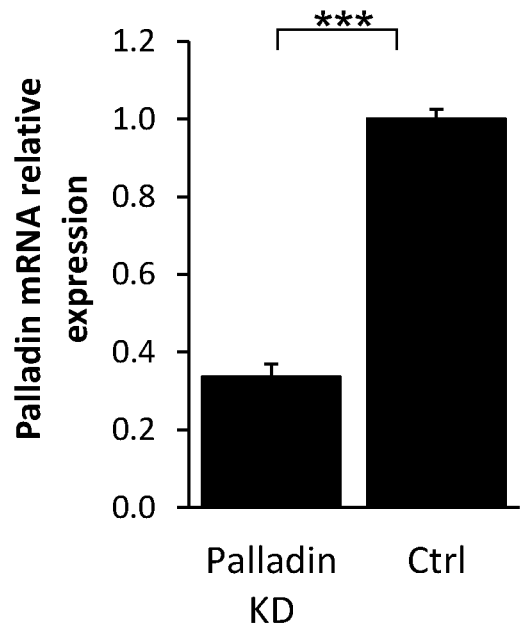
FIGS. 6A-D. Down-regulation of palladin mRNA.

Palladin mRNA and protein levels following stable over-expression of palladin shRNA were assayed. 4T1 cells were infected with palladin shRNA or a scrambled shRNA as control (Palladin shRNA target sequence: GCTAACCTAT-GAGGAAAGAAT (SEQ ID NO: 18)). Three (3) week later RNA was extracted from the cells and the level of palladin mRNA was measured by quantitative real-time PCR (qRT-PCR). The mRNA expression level was normalized to GAPDH. As shown in FIG. 6A, palladin mRNA was down-regulated in the palladin shRNA-infected cells (palladin knock-down (KD) cells) compared to cells infected with the control sequence (CCGGGCGCGATAGCGCTAATAA-TTTCTCGAGAAATTATTAGCGCTATCGCGCT TTTT (SEQ ID NO: 19)).

Figure 6B:
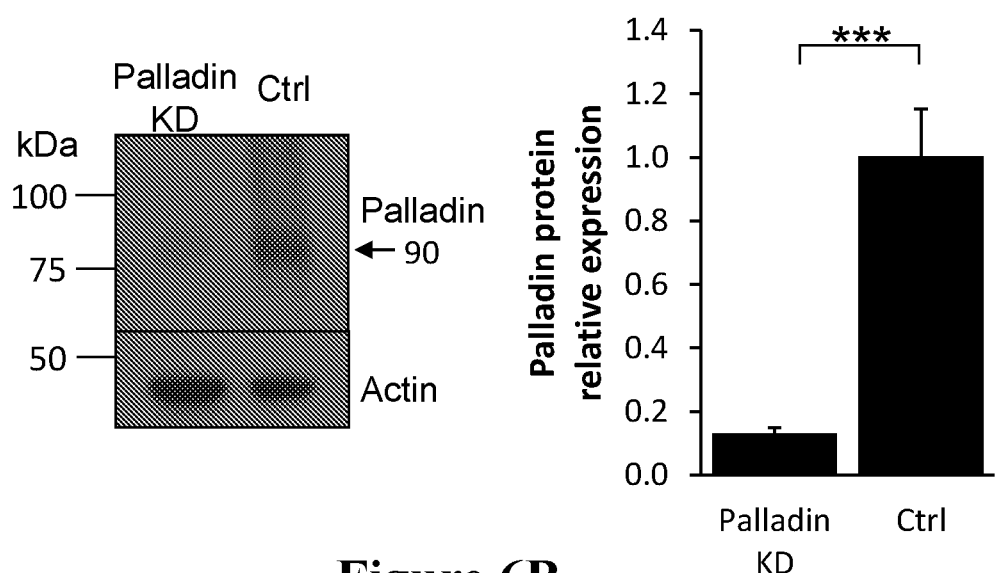

In addition, protein was extracted from the cells and the level of palladin protein (isoform 4, 90 kDa) was evaluated by Western blot (FIG. 6B, left panel). Bands quantification was done using ImageJ software and protein levels were normalized to Actin levels (FIG. 6B, right panel). Stable over-expression of palladin shRNA resulted in decreased palladin protein levels.

Figure 6C:
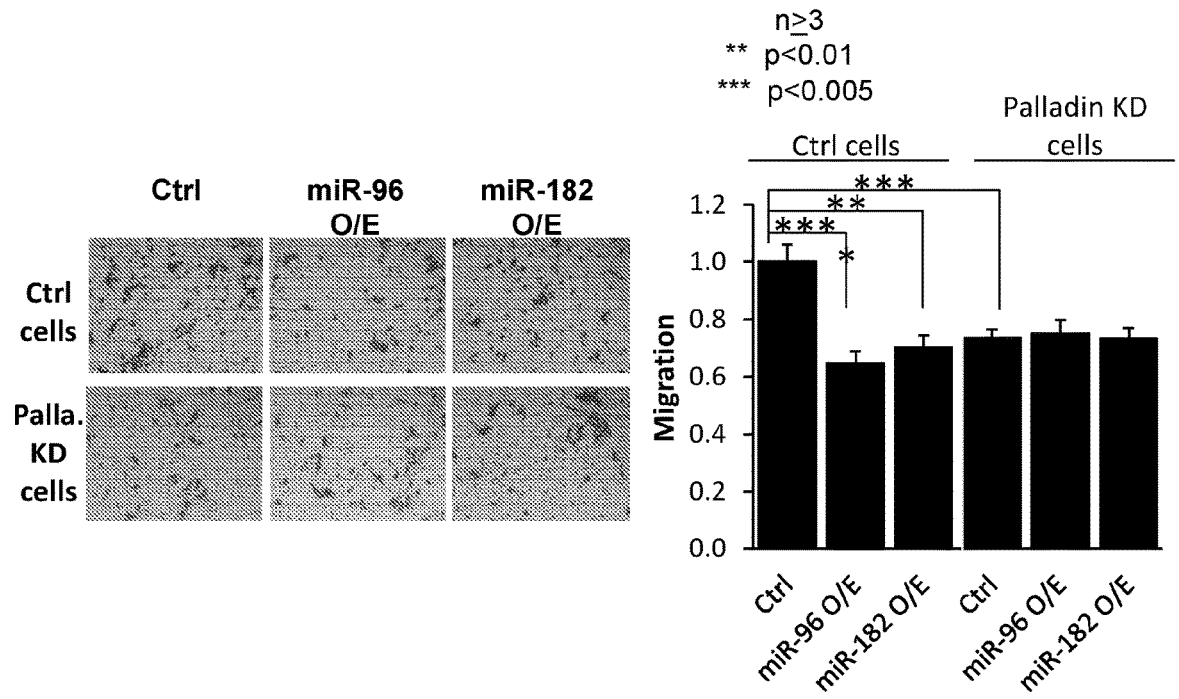
Figure 6D:
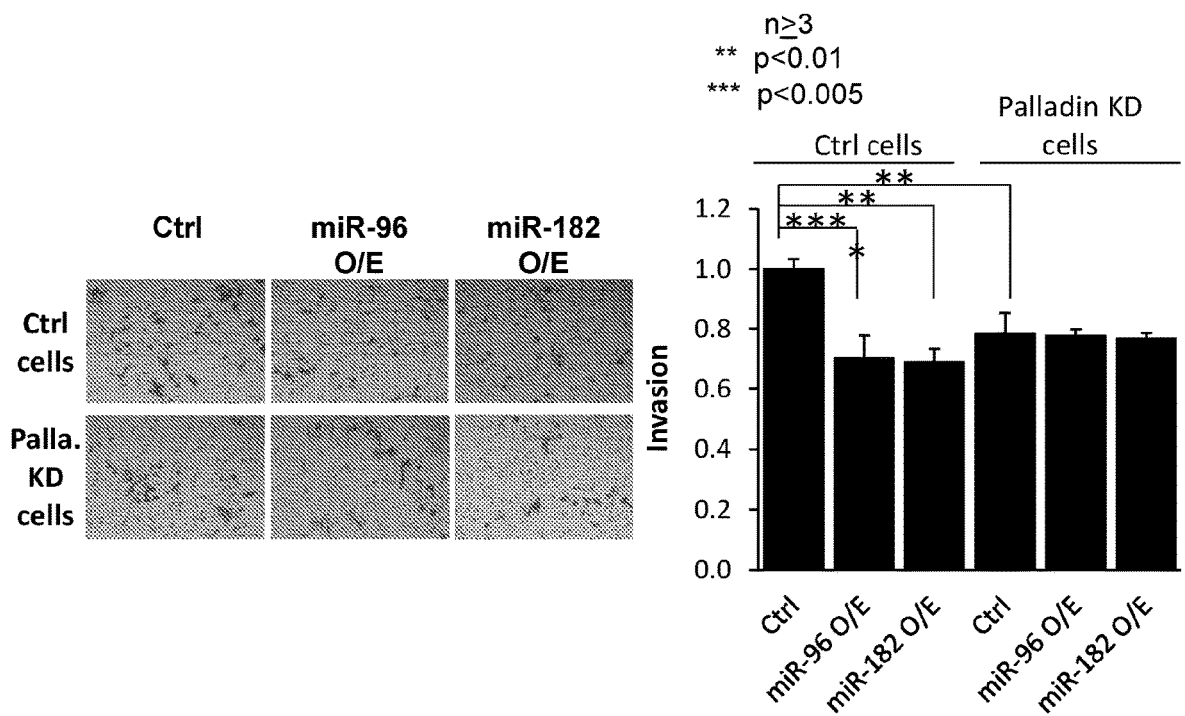

Cell migration and invasion following stable over-expression of palladin shRNA were also assayed. 4T1 cells stably expressing palladin shRNA (palladin KD cells) or a scrambled shRNA (control cells) were transfected with either miR-96, miR-182 or a scrambled control sequence. Transwell migration assay and Matrigel invasion assay were carried out 48 hours following transfection. The results are summarized in FIGS. 6C-D, respectively. Over-expression of miR-96 or miR-182, as well as stable expression of palladin shRNA, resulted in decreased cell migration and invasion.

Example 6—Effect of miR-96/miR-182 on Cell Proliferation Rate

Proliferation rate was determined in 4T1 cells 24-48 hours following transfection with miR-96, miR-182 or a scrambled control sequence using FITC BrdU Flow Kit (BD Biosciences). Anti FITC-BrdU and DAPI were used in order to determine the proportion of cells in each cell-cycle phase, and S/G1 ratios were calculated for each group. Proliferation rate was similarly determined in MCF-7 cells 24-48 hours following transfection with anti-miR-96, anti-miR-182 or a scrambled control sequence (n=3).

In addition, proliferation rate was determined 48 hours following transfection of Hs578 cells with miR-96, miR-182 or a scrambled control sequence using ViaLight Plus cell proliferation and cytotoxicity assay (Lonza) (n=4, * p<0.05).

Figure 7A:
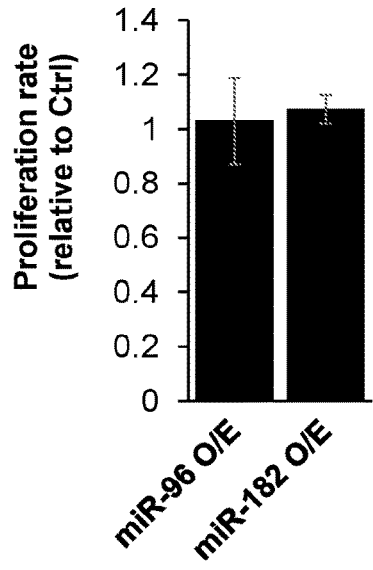
FIGS. 7A-C. Effect of over-expression of miR-96/miR-182 or anti-miR-96/anti-miR-182 on cell proliferation rate in 4T1 cells (FIG. 7A); MCF-7 cells (FIG. 7B); and Hs578 cells (FIG. 7C), transfected with the indicated miR. Paired student t-test was used for statistical analysis.
Figure 7B:
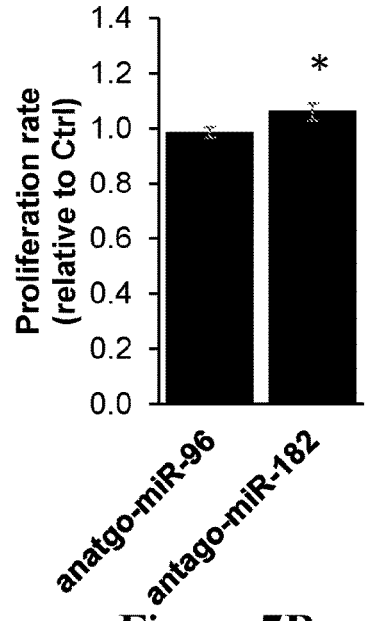
Figure 7C:
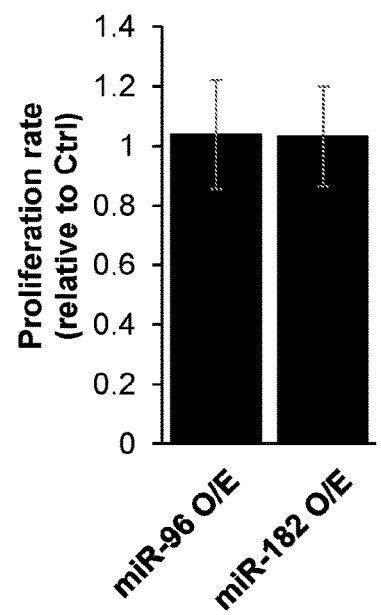

The results are summarized in FIGS. 7A-C, showing proliferation rates relative to control. Proliferation rate was not affected by miR-96/182 levels.

Example 7—Effect of miR-96/miR-182 on Tumor Metastasis In Vivo

Methods

The 4T1 mammary carcinoma is a transplantable tumor cell line. The tumor is typically grown in BALB/c mice and in tissue culture, and is highly tumorigenic and invasive. In addition, it can spontaneously metastasize from the primary tumor in the mammary gland to multiple distant sites including lymph nodes, blood, liver, lung, brain, and bone. In the present study, 4T1 cells constitutively expressing mCherry fluorescent protein and stably transformed with miR-96, miR-182 or a scrambled RNA were used. The constitutive expression of mCherry enables monitoring tumor growth and metastases spread in the mice, using an imaging system (CRI-MAESTRO™).

1. Maintaining 4T1 Tumor Cell Cultures In-Vitro.

The following growth medium was used:

| Reagent | Stock conc. | Final conc. | Dilution | Amount in 500 ml medium (ml) |
|---|---|---|---|---|
| RPM1 | | | | 431.7 |
| FBS | | 10% | 10 | 50 |
| L-glutamine (Biological industries) | | 1% | 100 | 5 |
| P/S (Penicillin/Streptomycin) (Biological industries) | 100 mg/ml | 100 ug/ml | 1000 | 0.5 |
| sodium pyruvate (Biological industries) | 100 mM | 1 mM | 100 | 5 |
| Hepes Buffer (Biological industries) | 1M | 10 mM | 100 | 5 |
| D-glucose (Sigma) | 450 g/L | 2.5 g/L | 180 | 2.8 |

Cells were incubated in a 37° C., 5% $CO_2$ tissue culture incubator. Cultures were split 2 to 3 times per week and were not allowed to exceed confluence (50% to 80%). For primary tumor growth, cultures that have been maintained for less than 2 months were used.

2. Harvesting 4T1 Tumor Cells for Injection.

Culture medium was discarded from the tissue culture plate. Next, 1 nil of 0.25% trypsin/1 mM EDTA solution was added and the plate was swirled such that the solution covers the entire plate. The plate was incubated with the trypsin/EDTA solution at room temperature for 2 min or at 37° C. in case cells were not dislodged from the plate. Following incubation, 9 nil PBS were added to harvest trypsinized cells from the plate. The cells were transferred to a 15-ml conical tube and centrifuged in a benchtop centrifuge for 4 min at 1200 rpm, room temperature. The supernatant was discarded and the pellet was re-suspended in PBS. Cell concentration was determined using a hemacytometer or cell-counter. Cells were then diluted with PBS to a concentration of $1 \times 10^7$ cells/ml and placed on ice.

3. Injecting Mice with Tumor Cells.

Female BALB/c mice (5-6 weeks old) were weighted and anesthetized by intraperitoneal (i.p) injection of 150 ul Ketamine-Xylazin solution. Next, 100 ul 4T1 cells ($1 \times 10^6$ cells) were injected subcutaneously into the mammary gland. Each group of mice (tumor cells over-expressing miR-96, miR-182 or a scrambled RNA) contained 6 mice.

4. Measuring Tumor Onset and Growth.

Tumor onset was monitored daily by palpating the injection area for the presence of a tumor. Mice weight and tumor size were checked every 3 to 4 days starting from day 5. Tumor size was determined by measuring two perpendicular measurements of the tumor (width and length) using Vernier caliper. The mean tumor diameter (TD) and the tumor volume (TV) were calculated.

5. Primary Tumor Removal.

Primary tumors were surgically removed when tumor measurements reached about 10×10 mm (length×width) or when tumors become necrotic. Prior to removal, the tumors were imaged using CRI-MAESTRO™ imaging system in order to measure fluorescent signals from the tumor and determine tumor area based on the fluorescence measurements. The removed tumors were weighted and stored in (−80°) C. for farther analyzes.

6. Monitoring Mice Survival.

Mice survival was monitored following tumor removal. The survival of the mice from the tumor inoculation date and the tumor removal date were tracked.

7. Quantification of Distant-Site Metastases.

One week following primary tumor removal (and about 3 weeks following tumor inoculation) the mice were weighted and anesthetized. The recurrence of the primary tumor was checked by imaging the primary tumor area using CRI-MAESTRO™ imaging system. If a fluorescent signal was detected at the primary tumor area, measurements of total fluorescent signal and tumor area were taken.

In order to check for macro-metastases presence, contrast dye was injected into the tail vein of each mouse and the mice were photographed using a computed tomography (CT) imaging system. The photographs included the brain, lungs and liver of the mice. The photographs were checked for the presence of metastases of a size around 0.5 mm (=macro-metastases). Mice were checked every 7 days until macro-metastases were detected. When macro-metastases were present in CT photos, mice were sacrificed and their lungs, brain and liver were removed and photographed by CRI-MAESTRO™ imaging system. In order to determine auto-florescence of each organ, organs of an untreated mouse were used.

Results

A. MiR Levels and Palladin Expression in the Primary Tumors

The primary tumors from mice injected with 4T1 cells stably transformed with either miR-96, miR-182 or a scrambled RNA molecule were analyzed for the levels of the respective miR, palladin mRNA and palladin protein. Following removal, all tumors were cut into a few pieces. One piece of each primary tumor was placed in an eppendorf tube containing Igepal lysis buffer for protein extraction, and another piece was placed in another eppendorf tube containing Trizol for RNA extraction. Tumors homogenization was done using TissueLayser (Qiagene). Measuring miRNA, mRNA and protein levels were done as mentioned above (example 2, pages 2-3).

The results are summarized in FIGS. 8A-D. As can be seen in the figures, the primary tumors originating from 4T1 cells expressing miR-96 or miR-182 showed increased expression of the respective miR concomitant with reduced levels of palladin mRNA and protein, compared to primary tumors originating from 4T1 cells expressing the scrambled RNA.

B. Parameters of the Primary Tumors

Figure 9A:
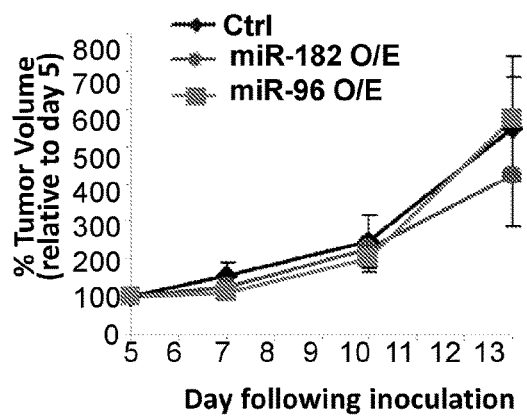
FIGS. 9A-F: Parameters of primary tumors in mice injected with 4T1 cells stably transformed with miR-96, miR-182 or a scrambled RNA molecule.
Figure 9B:
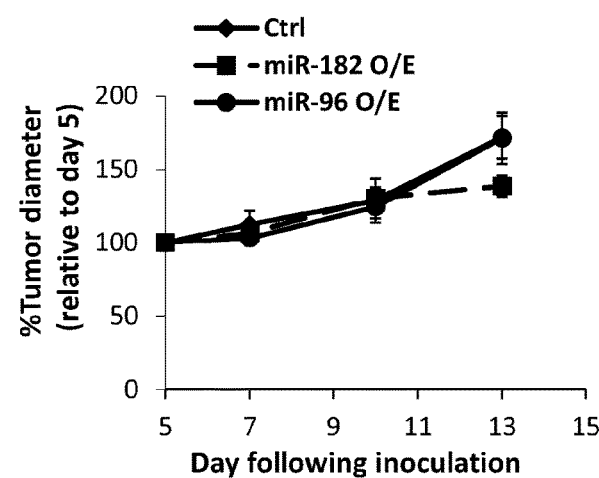
Figure 9C:
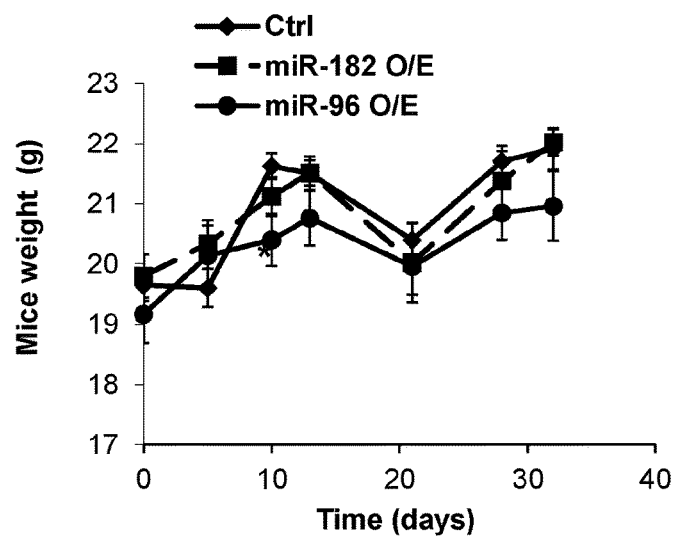

FIGS. 9A-C summarize measurements of tumor volume (FIG. 9A), tumor diameter (FIG. 9B) and mice weight (FIG. 9C) in each group of mice starting from day 5 following inoculation of the tumor cells.

Figure 9D:
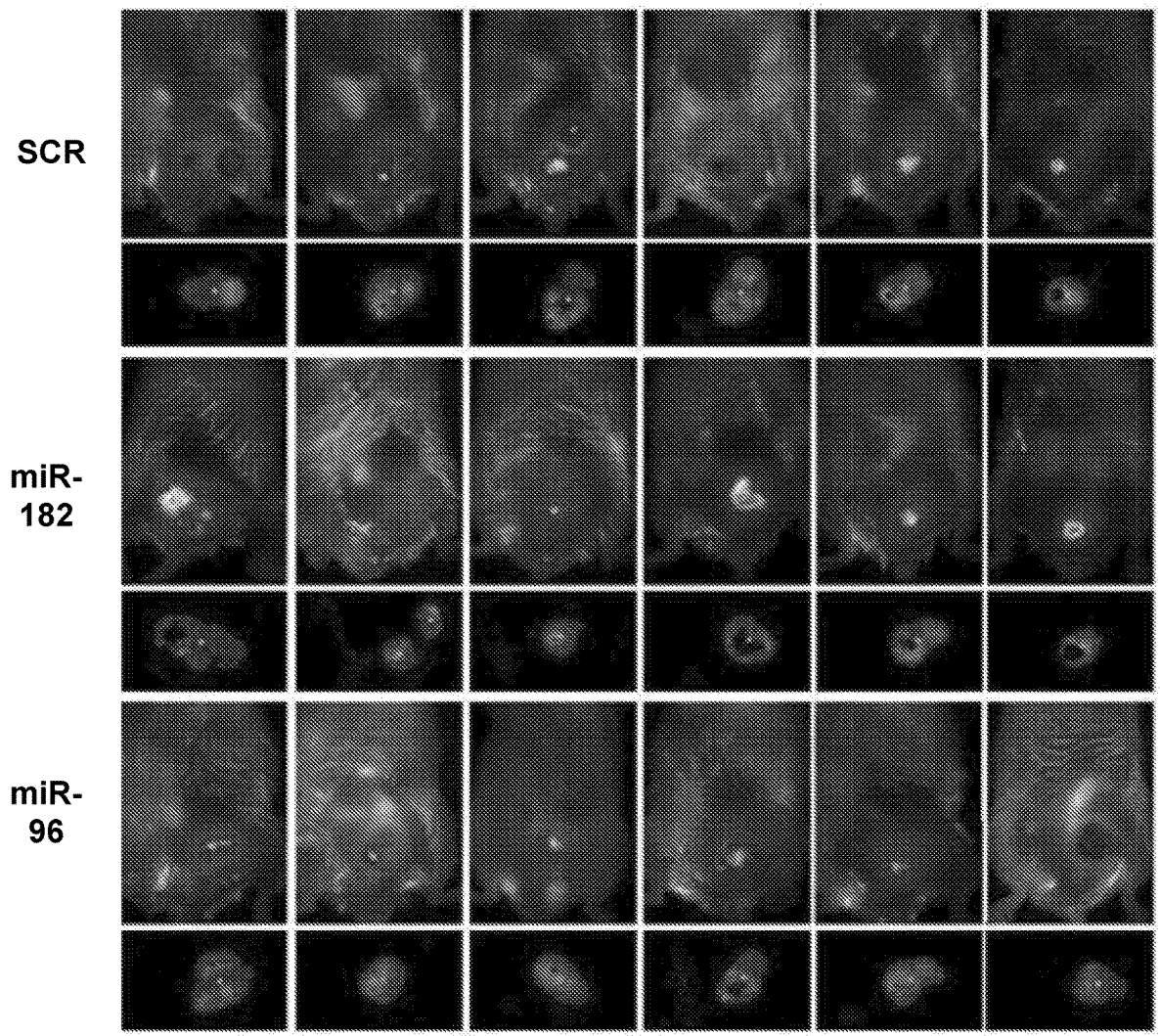

FIG. 9D shows exemplary fluorescence measurements of primary tumors from each group of mice at the removal day of the tumors. The upper panel of each group shows the total signal, and the lower panel shows the signal from the tumor area.

Figure 9E:
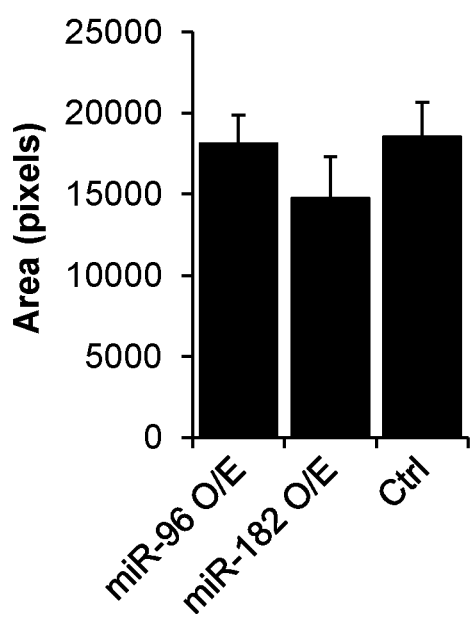
Figure 9F:
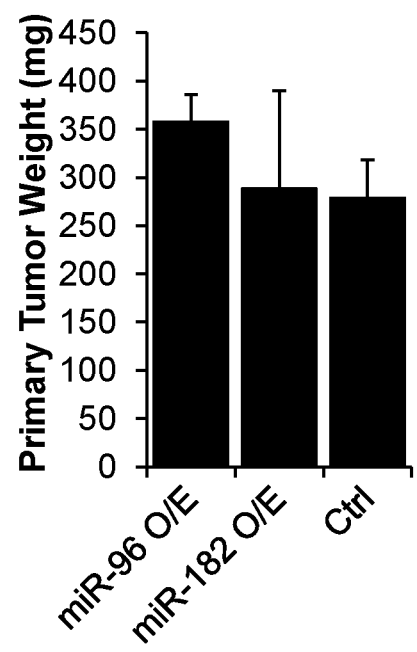

FIG. 9E shows the average tumor area of the primary tumors at their removal day in each group of mice, as determined from the fluorescence measurements. The average weights of the primary tumors at the day of their removal in each group are shown in FIG. 9F.

C. Establishment of Metastasis in the Lung

Figure 10A:
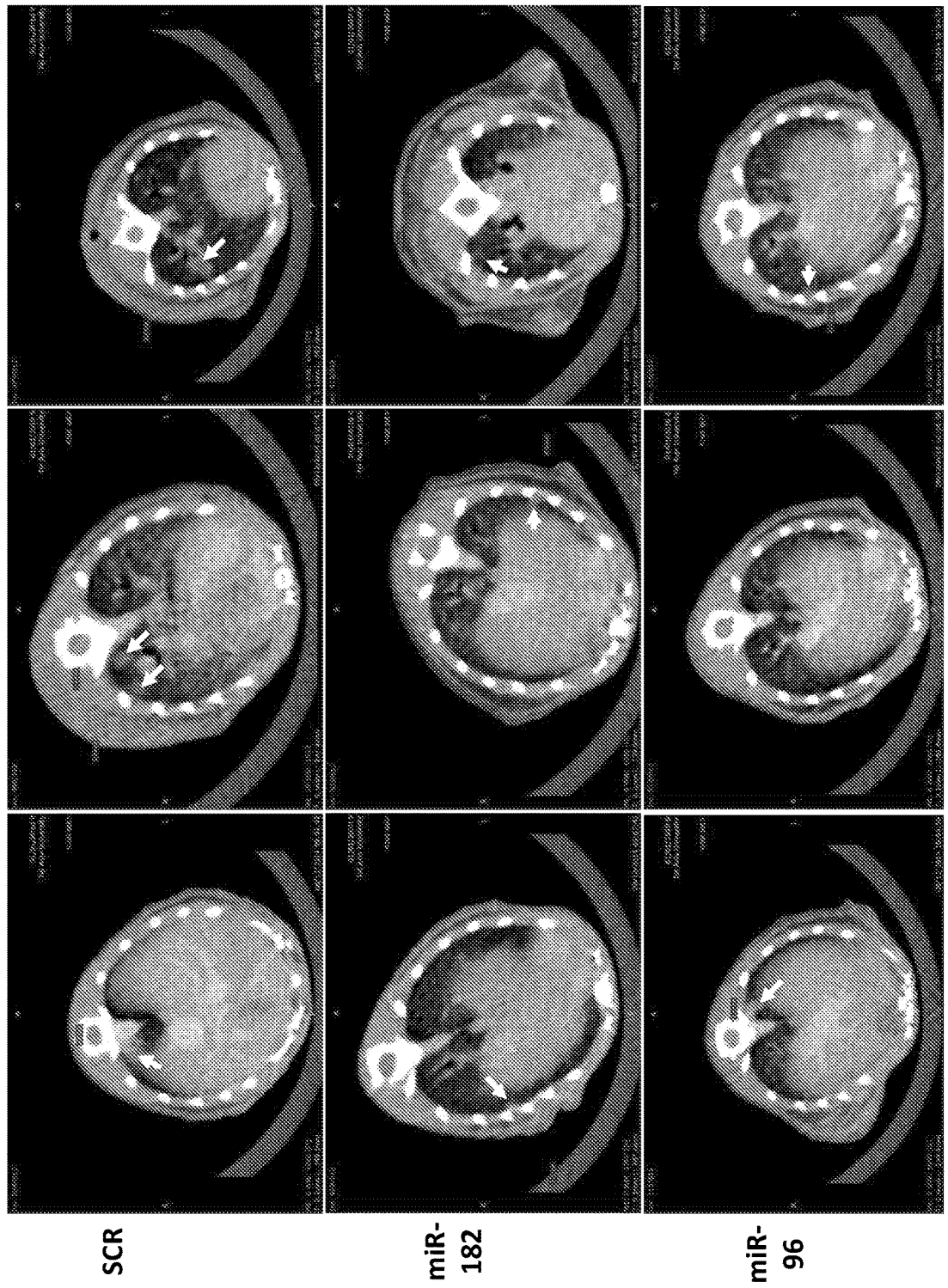

FIG. 10A shows exemplary CT photos of lungs from mice in each group. Metastatic nodules are marked with an arrow.

FIGS. 10B-C show the average quantity of lung metastatic nodules detected in the CT photos and the average diameter of lung metastases in each group of mice (no metastasis were detected in the brain or liver).

Figure 10D:
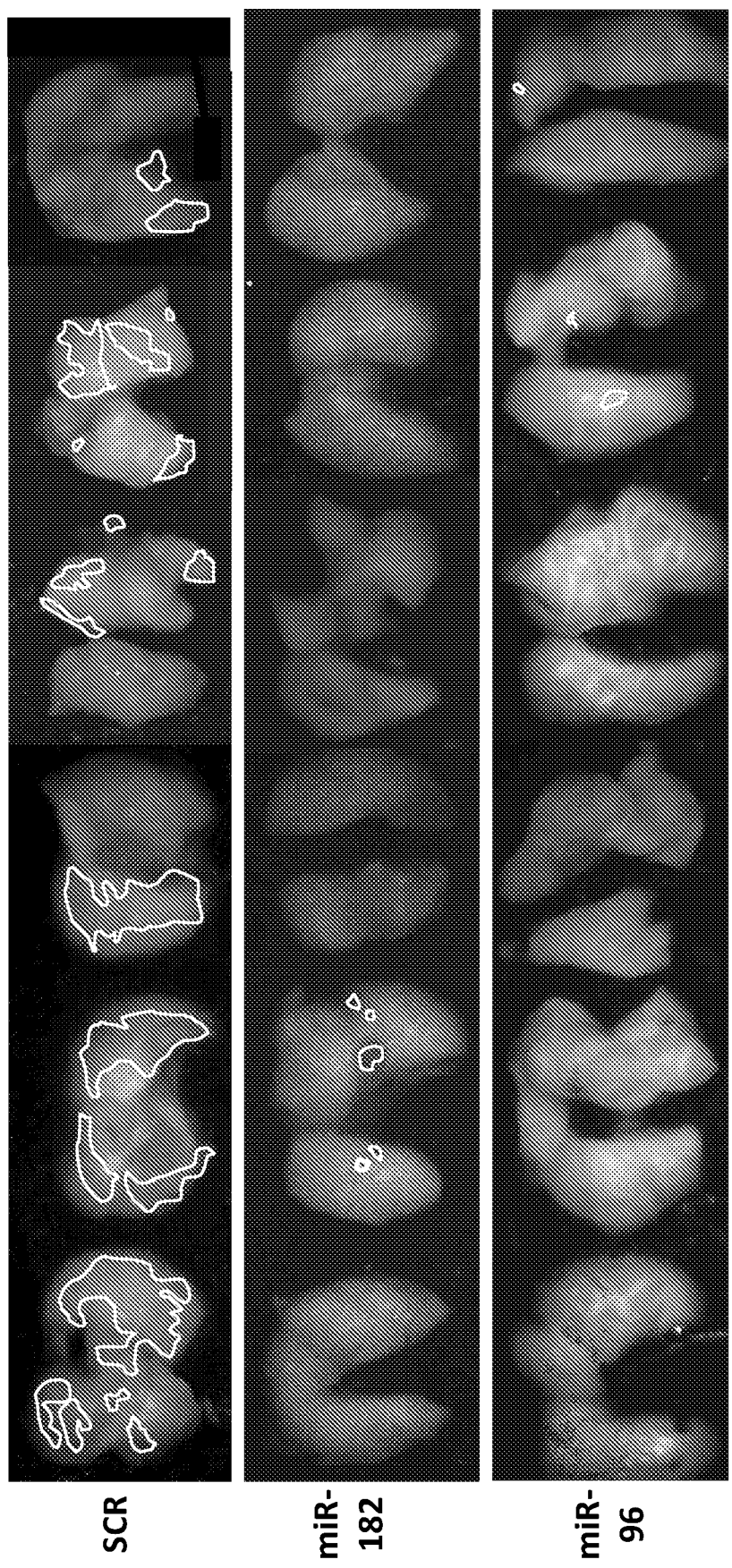
Figure 10E:
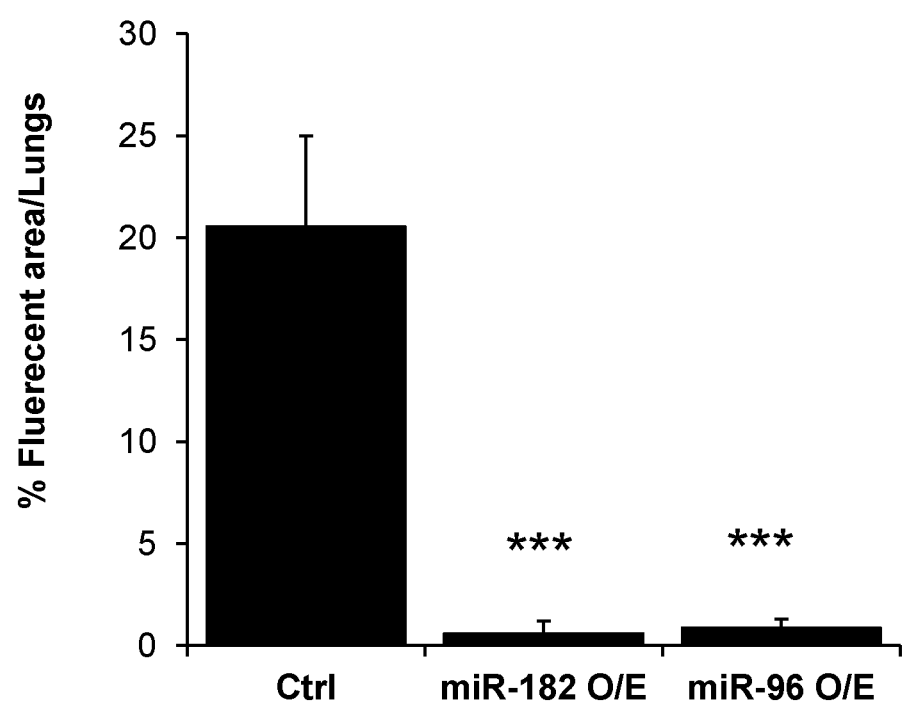

FIGS. 10D-E show exemplary fluorescence measurements in lungs and the average percentage of fluorescent area per lung in each group of mice. Metastatic areas are circled with white line.

As can be seen in the figures, over-expression of miR-96 or miR-182 in the tumor cells abolished almost completely the establishment of metastasis in the lungs, in contrast to the control construct composed of a scrambled RNA sequence. The results demonstrate the ability to use these miRs to inhibit metastasis formation in breast cancer patients.

Example 8—In-Vivo Delivery of miR-96/miR-182 Using Delivery Platforms

In order to achieve a specific and efficient in-vivo delivery of miR-96/182 to target tumor cells, as well as to metastases, with minimized delivery to other, non-target organs, several delivery systems, are utilized.

Dendritic Polyglycerolamine (dPG-NH$_2$) Nanocarriers— dPG-NH2 is a cationic hyperbranched polymer, which was shown to improve miRNA and siRNA stability, intracellular trafficking, silencing efficacy, and accumulation in the tumor environment due to the enhanced permeability and retention effect (Ofek P., et al. In vivo delivery of small interfering RNA to tumors and their vasculature by novel dendritic nanocarriers. FASEB J 2010; 24:3122-34.). dPG-NH2 was shown to exhibit low cytotoxicity and high efficacy in delivering active siRNA/miRNA into cells. To assess the in vivo therapeutic profile of dPG-NH2-miR-96/182, 4T1 mouse breast cancer cells are inoculated into the mammary fat pad of BALB/c female mice (BALB/cAnNCrl). Once palpable tumors develops, 10 mg/kg dPG-NH2 complexed with 4 mg/kg miR-96/182, NC-miR, or PBS is injected intratumorally every 3 days. Primary tumors are removed seven days after the first dPG-NH2-miRNA polyplex injection. The presence of metastases in the lungs is evaluated by micro-CT for additional twenty-one (21) days. Then, mice are sacrificed and the harvested organs (lungs, liver and brain) are screened for the presence of macro-metastases.

Targeted Liposomes—

Targeted liposomes encapsulating small RNAs are used, in combination with, or separately from other treatments. It was shown that stabilized liposomes can deliver siRNAs into leukocytes involved in gut inflammation to inhibit colitis in a mouse model (Peer, D., et al. Systemic leukocyte-directed siRNA delivery revealing cyclin D1 as an anti-inflammatory target. Science 2008; 319:5863). Antibodies targeting specific cancer cells (based on the receptors present on these cells, as determined, for example, by deep RNAseq analysis), are used as targeting moieties for delivering our the miRNAs molecules specifically to target cenacer cells and metastates, in order to effectively reduce the metastatic potential of the cells. The construct used is designed such that each liposome carries a high payload (~4000 siRNAs/miRNAs per particle), allowing therapeutic efficacy at a low dose (~2.5 mg/kg). The liposomal particles are coated with hyaluronan, a naturally occurring glycosaminoglycan that stabilizes small RNA entrapment, inhibits nonspecific uptake in vivo, and serves as the attachment site for the selected antibody. The effect of the treatments using these targeted liposomes on the tumor and metastasis is evaluated as described above.

Pentapeptide-Coupled Nanoparticles—

Nanoparticles (NPs) which carry the microRNA molecules, which are coupled to a pentapeptide which enhances binding to cancer cells and cancer metastatic cells are utilized. The pentapeptide, Tyr-Ile-Gly-Ser-Arg (YIGSR) (SEQ ID NO:14), derived from laminin β1 chain, the laminin binding site to its receptor, enhances nanoparticles targeting via interactions with the laminin receptor, whose expression is upregulated in various cancer cells and metastatic cells, including breast cancer (Sarfati G., et al. Targeting of polymeric nanoparticles to lung metastases by surface-attachment of YIGSR peptide from laminin Biomaterials. 2011; 32(1):152-61). The enhanced uptake of YIGSR-NPs by lung cancer cells and metastatic cells in vitro and in vivo has been previously shown in a mouse model. A fluorescent nanoparticles (such as, Estapor® F1-XC030 (299±6 nm in diameter), encapsulating a green fluorescent dye (Merck)), is used. Treatment using the pentapeptide nanoparticles is given intravenous via the tail vein and the effect of the treatments on the tumor and metastasis is evaluated as described above.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for reducing or preventing cancer metastasis in a subject in need thereof, the method comprising administering to the subject at least one miRNA molecule selected from the group consisting of miR-96 and miR-182, or at least one vector expressing or encoding the same, thereby reducing or preventing cancer metastasis in the subject, wherein the subject is carrying the C allele of the single nucleotide polymorphism (SNP) rs1071738 within the gene PALLD.

2. The method of claim 1, wherein the subject is at risk of developing metastasis and the administering is carried out prior to metastasis formation.

3. The method of claim 1, wherein the subject has already developed metastases and the administering is carried out after metastasis formation.

4. The method of claim 1, wherein the cancer is a cancer associated with an abnormal palladin expression and/or activity.

5. The method of claim 1, wherein the cancer is selected from the group consisting of breast cancer, pancreatic cancer and colorectal cancer.

6. The method of claim 1, wherein the cancer is breast cancer.

7. The method of claim 1, wherein the method comprises administering a miR-96 molecule and a miR-182 molecule, or one or more vectors expressing or encoding the miR-96 and miR-182 molecules.

8. The method of claim 7, wherein the miR-96 molecule and the miR-182 molecule, or the vectors expressing or encoding the same, are administered concomitantly.

9. The method of claim 7, wherein the miR-96 molecule and the miR-182 molecule, or the vectors expressing or encoding the same, are administered sequentially.

10. The method of claim 1, wherein the miR-96 is a mature miR-96 as set forth in SEQ ID NO: 1.

11. The method of claim 1, wherein the miR-96 is a precursor of miR-96.

12. The method of claim 11, wherein the precursor of miR-96 is a pri-miRNA as set forth in SEQ ID NO: 2.

13. The method of claim 11, wherein the precursor of miR-96 is a pre-miRNA as set forth in SEQ ID NO: 3.

14. The method of claim 1, wherein the miR-182 is a mature miR-182 as set forth in SEQ ID NO: 4.

15. The method of claim 1, wherein the miR-182 is a precursor of miR-182.

16. The method of claim 15, wherein the precursor of miR-182 is a pri-miRNA as set forth in SEQ ID NO: 5.

17. The method of claim 15, wherein the precursor of miR-182 is a pre-miRNA as set forth in SEQ ID NO: 6.

18. The method of claim 1, wherein the at least one miRNA molecule or vector expressing or encoding the same is formulated in a pharmaceutical composition with a pharmaceutically acceptable carrier.

19. The method of claim 1, wherein the administering is administering systemically.

20. The method of claim 1, wherein the administering is administering locally.

21. The method of claim 20, wherein administering locally is administering into a tumor.

22. The method of claim 20, wherein administering locally is administering into a space or cavity adjacent to a tumor.

23. The method of claim 20, wherein administering locally is administering into a space or cavity formed after tumor resection.

* * * * *